United States Patent
Lipman et al.

(10) Patent No.: US 11,986,293 B2
(45) Date of Patent: May 21, 2024

(54) MEDICAL DIAGNOSTIC DEVICES AND METHODS

(71) Applicant: Intuity Medical, Inc., Fremont, CA (US)

(72) Inventors: Kelley J. Lipman, Livermore, CA (US); Michael F. Tomasco, Morgan Hill, CA (US); Daniel N. Brncic, Menlo Park, CA (US); David K. Hohl, Milpitas, CA (US); Paul D. Reynolds, Palo Alto, CA (US); Raul Escutia, Sunnyvale, CA (US)

(73) Assignee: Intuity Medical, Inc., Fremont, CA (US)

( * ) Notice: Subject to any disclaimer, the term of this patent is extended or adjusted under 35 U.S.C. 154(b) by 0 days.

(21) Appl. No.: 18/067,135

(22) Filed: Dec. 16, 2022

(65) Prior Publication Data

US 2023/0123209 A1    Apr. 20, 2023

Related U.S. Application Data

(63) Continuation of application No. 16/536,066, filed on Aug. 8, 2019, now Pat. No. 11,553,860, which is a continuation of application No. 12/457,332, filed on Jun. 8, 2009, now Pat. No. 10,383,556.

(60) Provisional application No. 61/129,148, filed on Jun. 6, 2008.

(51) Int. Cl.
*A61B 5/00*    (2006.01)
*A61B 5/145*    (2006.01)
*C12Q 1/54*    (2006.01)

(52) U.S. Cl.
CPC ........ *A61B 5/14532* (2013.01); *A61B 5/0002* (2013.01); *C12Q 1/54* (2013.01)

(58) Field of Classification Search
CPC ............................. A61B 5/14532; C12Q 1/54
See application file for complete search history.

(56) References Cited

U.S. PATENT DOCUMENTS

| | | | |
|---|---|---|---|
| 842,690 | A | 1/1907 | Oswalt |
| D137,874 | S | 5/1944 | Charles |
| 2,749,797 | A | 6/1956 | Harks |
| 3,092,465 | A | 6/1963 | Adams, Jr. et al. |
| 3,310,002 | A | 3/1967 | Wilburn |
| 3,620,209 | A | 11/1971 | Kravitz |
| 3,623,475 | A | 11/1971 | Sanz et al. |
| 3,626,929 | A | 12/1971 | Sanz et al. |

(Continued)

FOREIGN PATENT DOCUMENTS

| | | |
|---|---|---|
| CA | 2201530 A1 | 9/1997 |
| CA | 2513465 A1 | 8/2004 |

(Continued)

OTHER PUBLICATIONS

ADA Consensus Development Panel. (Jan.-Feb. 1987). "Consensus Statement on Self-Monitoring of Blood Glucose," Diabetes Care 10(1):95-99.

(Continued)

*Primary Examiner* — Phuong Chi Thi Nguyen
(74) *Attorney, Agent, or Firm* — COOLEY LLP (57) ABSTRACT

A medical diagnostic device includes a wirelessly transmitted time data receiver and processor. Associated devices, methods and functionality are also described.

22 Claims, 3 Drawing Sheets

(56) References Cited

U.S. PATENT DOCUMENTS

| | | |
|---|---|---|
| 3,630,957 A | 12/1971 | Rey et al. |
| D223,165 S | 3/1972 | Michael |
| 3,723,064 A | 3/1973 | Liotta et al. |
| 3,741,197 A | 6/1973 | Sanz et al. |
| 3,961,898 A | 6/1976 | Neeley et al. |
| 3,992,158 A | 11/1976 | Przybylowicz et al. |
| 4,014,328 A | 3/1977 | Cluff et al. |
| 4,042,335 A | 8/1977 | Clement |
| 4,057,394 A | 11/1977 | Genshaw |
| 4,109,655 A | 8/1978 | Chacornac |
| 4,250,257 A | 2/1981 | Lee et al. |
| 4,253,083 A | 2/1981 | Imamura |
| 4,254,083 A | 3/1981 | Columbus |
| 4,258,001 A | 3/1981 | Pierce et al. |
| 4,260,257 A | 4/1981 | Neeley et al. |
| 4,289,459 A | 9/1981 | Neeley et al. |
| 4,321,397 A | 3/1982 | Nix et al. |
| 4,350,762 A | 9/1982 | De Luca et al. |
| 4,394,512 A | 7/1983 | Batz |
| 4,414,975 A | 11/1983 | Ryder et al. |
| 4,416,279 A | 11/1983 | Lindner et al. |
| 4,418,037 A | 11/1983 | Katsuyama et al. |
| 4,422,941 A | 12/1983 | Vaughan, Jr. et al. |
| 4,429,700 A | 2/1984 | Thees et al. |
| 4,627,445 A | 12/1986 | Garcia et al. |
| 4,637,403 A | 1/1987 | Garcia et al. |
| 4,637,406 A | 1/1987 | Guinn et al. |
| 4,653,513 A | 3/1987 | Dombrowski |
| 4,661,319 A | 4/1987 | Lape |
| 4,702,261 A | 10/1987 | Cornell et al. |
| 4,711,250 A | 12/1987 | Gilbaugh, Jr. et al. |
| 4,737,458 A | 4/1988 | Batz et al. |
| 4,747,687 A | 5/1988 | Hoppe et al. |
| 4,767,415 A | 8/1988 | Duffy |
| 4,774,192 A | 9/1988 | Terminiello et al. |
| 4,787,398 A | 11/1988 | Garcia et al. |
| 4,790,979 A | 12/1988 | Terminiello et al. |
| 4,794,926 A | 1/1989 | Munsch et al. |
| 4,815,843 A | 3/1989 | Tiefenthaler et al. |
| 4,829,470 A | 5/1989 | Wang |
| 4,844,095 A | 7/1989 | Chiodo et al. |
| 4,846,785 A | 7/1989 | Cassou et al. |
| 4,887,306 A | 12/1989 | Hwang et al. |
| 4,920,977 A | 5/1990 | Haynes |
| 4,929,426 A | 5/1990 | Bodai et al. |
| 4,930,525 A | 6/1990 | Palestrant |
| 4,935,346 A | 6/1990 | Phillips et al. |
| 4,953,552 A | 9/1990 | DeMarzo |
| 4,966,646 A | 10/1990 | Zdeblick |
| 4,983,178 A | 1/1991 | Schnell |
| 4,995,402 A | 2/1991 | Smith et al. |
| 5,026,388 A | 6/1991 | Ingalz |
| 5,029,583 A | 7/1991 | Meserol et al. |
| 5,035,704 A | 7/1991 | Lambert et al. |
| 5,037,199 A | 8/1991 | Hlousek |
| 5,049,487 A | 9/1991 | Phillips et al. |
| 5,050,617 A | 9/1991 | Columbus et al. |
| 5,054,878 A | 10/1991 | Gergely et al. |
| 5,059,394 A | 10/1991 | Phillips et al. |
| 5,077,199 A | 12/1991 | Basagni et al. |
| 5,094,943 A | 3/1992 | Siedel et al. |
| 5,110,724 A | 5/1992 | Hewett |
| 5,114,350 A | 5/1992 | Hewett |
| 5,116,759 A | 5/1992 | Klainer et al. |
| 5,131,404 A | 7/1992 | Neeley et al. |
| 5,141,868 A | 8/1992 | Shanks et al. |
| 5,145,565 A | 9/1992 | Kater et al. |
| 5,146,437 A | 9/1992 | Boucheron |
| 5,153,416 A | 10/1992 | Neeley |
| 5,164,575 A | 11/1992 | Neeley et al. |
| 5,166,498 A | 11/1992 | Neeley |
| 5,174,291 A | 12/1992 | Schoonen et al. |
| 5,176,632 A | 1/1993 | Bernardi |
| 5,179,005 A | 1/1993 | Phillips et al. |
| 5,183,741 A | 2/1993 | Arai et al. |
| 5,194,393 A | 3/1993 | Hugl et al. |
| 5,196,302 A | 3/1993 | Kidwell |
| 5,208,163 A | 5/1993 | Charlton et al. |
| 5,213,966 A | 5/1993 | Vuorinen et al. |
| 5,217,480 A | 6/1993 | Haber et al. |
| 5,218,966 A | 6/1993 | Yamasawa |
| 5,223,219 A | 6/1993 | Subramanian et al. |
| 5,228,972 A | 7/1993 | Osaka et al. |
| 5,234,818 A | 8/1993 | Zimmermann et al. |
| 5,241,969 A | 9/1993 | Carson et al. |
| 5,251,126 A | 10/1993 | Kahn et al. |
| D341,848 S | 11/1993 | Bigelow et al. |
| 5,269,800 A | 12/1993 | Davis, Jr. |
| 5,275,159 A | 1/1994 | Griebel |
| 5,278,079 A | 1/1994 | Gubinski et al. |
| 5,279,294 A | 1/1994 | Anderson et al. |
| 5,288,646 A | 2/1994 | Lundsgaard et al. |
| 5,299,571 A | 4/1994 | Mastrototaro |
| 5,301,686 A | 4/1994 | Newman |
| 5,302,513 A | 4/1994 | Miike et al. |
| 5,304,468 A | 4/1994 | Phillips et al. |
| 5,306,623 A | 4/1994 | Kiser et al. |
| 5,308,767 A | 5/1994 | Terashima |
| 5,314,441 A | 5/1994 | Cusack et al. |
| 5,320,607 A | 6/1994 | Ishibashi |
| 5,354,537 A | 10/1994 | Moreno |
| 5,360,595 A | 11/1994 | Bell et al. |
| 5,368,047 A | 11/1994 | Suzuki et al. |
| 5,383,512 A | 1/1995 | Jarvis |
| 5,390,671 A | 2/1995 | Lord et al. |
| 5,399,316 A | 3/1995 | Yamada |
| 5,401,110 A | 3/1995 | Neeley |
| 5,402,798 A | 4/1995 | Swierczek et al. |
| 5,426,032 A | 6/1995 | Phillips et al. |
| 5,441,513 A | 8/1995 | Roth |
| 5,451,350 A | 9/1995 | Macho et al. |
| 5,458,140 A | 10/1995 | Eppstein et al. |
| 5,460,777 A | 10/1995 | Kitajima et al. |
| 5,460,968 A | 10/1995 | Yoshida et al. |
| 5,482,473 A | 1/1996 | Lord et al. |
| 5,489,414 A | 2/1996 | Schreiber et al. |
| 5,506,200 A | 4/1996 | Hirschkoff et al. |
| 5,507,288 A | 4/1996 | Bocker et al. |
| 5,508,200 A | 4/1996 | Tiffany et al. |
| 5,510,266 A | 4/1996 | Bonner et al. |
| 5,514,152 A | 5/1996 | Smith |
| 5,518,689 A | 5/1996 | Dosmann et al. |
| 5,525,518 A | 6/1996 | Lundsgaard et al. |
| 5,527,892 A | 6/1996 | Borsotti et al. |
| 5,563,042 A | 10/1996 | Phillips et al. |
| 5,568,806 A | 10/1996 | Cheney, II et al. |
| 5,569,287 A | 10/1996 | Tezuka et al. |
| 5,575,403 A | 11/1996 | Charlton et al. |
| 5,577,499 A | 11/1996 | Teves |
| 5,582,184 A | 12/1996 | Erickson et al. |
| 5,586,553 A | 12/1996 | Halili et al. |
| 5,591,139 A | 1/1997 | Lin et al. |
| 5,593,838 A | 1/1997 | Zanzucchi et al. |
| 5,602,647 A | 2/1997 | Xu et al. |
| 5,611,809 A | 3/1997 | Marshall et al. |
| 5,611,999 A | 3/1997 | Dosmann et al. |
| 5,624,458 A | 4/1997 | Lipscher |
| 5,630,986 A | 5/1997 | Charlton et al. |
| 5,632,410 A | 5/1997 | Moulton et al. |
| 5,636,632 A | 6/1997 | Bommannan et al. |
| 5,638,828 A | 6/1997 | Lauks et al. |
| 5,647,851 A | 7/1997 | Pokras |
| 5,658,515 A | 8/1997 | Lee et al. |
| 5,660,791 A | 8/1997 | Brenneman et al. |
| 5,670,031 A | 9/1997 | Hintsche et al. |
| 5,676,850 A | 10/1997 | Reed et al. |
| 5,680,858 A | 10/1997 | Hansen et al. |
| 5,681,484 A | 10/1997 | Zanzucchi et al. |
| 5,682,233 A | 10/1997 | Brinda |
| 5,697,901 A | 12/1997 | Eriksson |
| 5,700,695 A | 12/1997 | Yassinzadeh et al. |
| 5,701,181 A | 12/1997 | Boiarski et al. |
| 5,701,910 A | 12/1997 | Powles et al. |
| D389,761 S | 1/1998 | Thomas |

(56) References Cited

U.S. PATENT DOCUMENTS

| | | |
|---|---|---|
| 5,705,018 A | 1/1998 | Hartley |
| 5,708,247 A | 1/1998 | McAleer et al. |
| 5,708,787 A | 1/1998 | Nakano et al. |
| 5,715,417 A | 2/1998 | Gardien et al. |
| 5,730,753 A | 3/1998 | Morita |
| 5,735,273 A | 4/1998 | Kurnik et al. |
| 5,736,103 A | 4/1998 | Pugh |
| 5,741,211 A | 4/1998 | Renirie et al. |
| 5,746,217 A | 5/1998 | Erickson et al. |
| 5,746,720 A | 5/1998 | Stouder, Jr. |
| 5,753,452 A | 5/1998 | Smith |
| 5,757,666 A | 5/1998 | Schreiber et al. |
| 5,759,364 A | 6/1998 | Charlton et al. |
| 5,766,066 A | 6/1998 | Ranniger |
| 5,771,890 A | 6/1998 | Tamada |
| 5,789,255 A | 8/1998 | Yu |
| 5,797,693 A | 8/1998 | Jaeger |
| 5,800,420 A | 9/1998 | Gross et al. |
| 5,801,057 A | 9/1998 | Smart et al. |
| 5,807,375 A | 9/1998 | Gross et al. |
| 5,820,570 A | 10/1998 | Erickson et al. |
| 5,827,183 A | 10/1998 | Kurnik et al. |
| 5,840,020 A | 11/1998 | Heinonen et al. |
| 5,841,126 A | 11/1998 | Fossum et al. |
| 5,843,692 A | 12/1998 | Phillips et al. |
| 5,846,837 A | 12/1998 | Thym et al. |
| 5,851,215 A | 12/1998 | Mawhirt et al. |
| 5,854,074 A | 12/1998 | Charlton et al. |
| D403,975 S | 1/1999 | Douglas et al. |
| 5,855,801 A | 1/1999 | Lin et al. |
| 5,856,195 A | 1/1999 | Charlton et al. |
| 5,858,194 A | 1/1999 | Bell |
| 5,866,281 A | 2/1999 | Guckel et al. |
| 5,866,349 A | 2/1999 | Lilja et al. |
| 5,871,494 A | 2/1999 | Simons et al. |
| 5,879,310 A | 3/1999 | Sopp et al. |
| 5,879,326 A | 3/1999 | Godshall et al. |
| 5,879,367 A | 3/1999 | Latterell et al. |
| 5,885,839 A | 3/1999 | Lingane et al. |
| 5,891,053 A | 4/1999 | Sesekura |
| 5,893,870 A | 4/1999 | Talen et al. |
| D411,621 S | 6/1999 | Eisenbarth et al. |
| 5,911,711 A | 6/1999 | Pelkey |
| 5,911,737 A | 6/1999 | Lee et al. |
| 5,912,139 A | 6/1999 | Iwata et al. |
| 5,925,021 A | 7/1999 | Castellano et al. |
| 5,926,271 A | 7/1999 | Couderc et al. |
| 5,928,207 A | 7/1999 | Pisano et al. |
| 5,930,873 A | 8/1999 | Wyser |
| 5,938,679 A | 8/1999 | Freeman et al. |
| 5,945,678 A | 8/1999 | Yanagisawa |
| 5,951,492 A | 9/1999 | Douglas et al. |
| 5,951,493 A | 9/1999 | Douglas et al. |
| 5,951,521 A | 9/1999 | Mastrototaro et al. |
| 5,954,685 A | 9/1999 | Tierney |
| 5,962,215 A | 10/1999 | Douglas et al. |
| 5,968,760 A | 10/1999 | Phillips et al. |
| 5,968,765 A | 10/1999 | Grage et al. |
| 5,968,836 A | 10/1999 | Matzinger et al. |
| 5,971,941 A | 10/1999 | Simons et al. |
| 5,972,294 A | 10/1999 | Smith et al. |
| 5,986,754 A | 11/1999 | Harding |
| 5,989,409 A | 11/1999 | Kurnik et al. |
| 5,993,189 A | 11/1999 | Mueller et al. |
| D417,504 S | 12/1999 | Love et al. |
| 6,001,067 A | 12/1999 | Shults et al. |
| 6,005,545 A | 12/1999 | Nishida et al. |
| 6,010,463 A | 1/2000 | Lauks et al. |
| 6,010,519 A | 1/2000 | Mawhirt et al. |
| 6,014,135 A | 1/2000 | Fernandes |
| 6,014,577 A | 1/2000 | Henning et al. |
| 6,015,969 A | 1/2000 | Nathel et al. |
| 6,023,629 A | 2/2000 | Tamada |
| 6,027,459 A | 2/2000 | Shain et al. |
| 6,030,827 A | 2/2000 | Davis et al. |
| 6,032,059 A | 2/2000 | Henning et al. |
| 6,036,924 A | 3/2000 | Simons et al. |
| 6,041,253 A | 3/2000 | Kost et al. |
| 6,045,753 A | 4/2000 | Loewy et al. |
| 6,048,352 A | 4/2000 | Douglas et al. |
| 6,050,988 A | 4/2000 | Zuck |
| 6,056,701 A | 5/2000 | Duchon et al. |
| 6,056,734 A | 5/2000 | Jacobsen et al. |
| 6,058,321 A | 5/2000 | Swayze et al. |
| 6,059,815 A | 5/2000 | Lee et al. |
| 6,061,128 A | 5/2000 | Zweig et al. |
| 6,063,039 A | 5/2000 | Cunningham et al. |
| 6,071,251 A | 6/2000 | Cunningham et al. |
| 6,071,294 A | 6/2000 | Simons et al. |
| 6,077,660 A | 6/2000 | Wong et al. |
| 6,080,116 A | 6/2000 | Erickson et al. |
| 6,083,196 A | 7/2000 | Trautman et al. |
| 6,086,544 A | 7/2000 | Hibner et al. |
| 6,090,790 A | 7/2000 | Eriksson |
| 6,091,975 A | 7/2000 | Daddona et al. |
| 6,093,156 A | 7/2000 | Cunningham et al. |
| 6,097,831 A | 8/2000 | Wieck et al. |
| 6,099,484 A | 8/2000 | Douglas et al. |
| 6,100,107 A | 8/2000 | Lei et al. |
| 6,102,933 A | 8/2000 | Lee et al. |
| 6,103,033 A | 8/2000 | Say et al. |
| 6,103,197 A | 8/2000 | Werner |
| 6,106,751 A | 8/2000 | Talbot et al. |
| 6,118,126 A | 9/2000 | Zanzucchi |
| 6,120,676 A | 9/2000 | Heller et al. |
| 6,121,050 A | 9/2000 | Han |
| 6,123,861 A | 9/2000 | Santini, Jr. et al. |
| 6,126,899 A | 10/2000 | Woudenberg et al. |
| 6,132,449 A | 10/2000 | Lum et al. |
| 6,139,562 A | 10/2000 | Mauze et al. |
| 6,142,939 A | 11/2000 | Eppstein et al. |
| 6,152,942 A | 11/2000 | Brenneman et al. |
| 6,162,639 A | 12/2000 | Douglas |
| 6,172,743 B1 | 1/2001 | Kley et al. |
| 6,175,752 B1 | 1/2001 | Say et al. |
| 6,176,865 B1 | 1/2001 | Mauze et al. |
| 6,183,434 B1 | 2/2001 | Eppstein |
| 6,183,489 B1 | 2/2001 | Douglas et al. |
| 6,184,990 B1 | 2/2001 | Amirkhanian et al. |
| 6,187,210 B1 | 2/2001 | Lebouitz et al. |
| 6,192,891 B1 | 2/2001 | Gravel et al. |
| 6,193,873 B1 | 2/2001 | Ohara et al. |
| 6,197,257 B1 | 3/2001 | Raskas |
| 6,200,296 B1 | 3/2001 | Dibiasi et al. |
| 6,206,841 B1 | 3/2001 | Cunningham et al. |
| 6,214,626 B1 | 4/2001 | Meller et al. |
| 6,219,574 B1 | 4/2001 | Cormier et al. |
| 6,228,100 B1 | 5/2001 | Schraga |
| 6,230,051 B1 | 5/2001 | Cormier et al. |
| 6,231,531 B1 | 5/2001 | Lum et al. |
| 6,241,862 B1 | 6/2001 | McAleer et al. |
| 6,242,207 B1 | 6/2001 | Douglas et al. |
| 6,245,215 B1 | 6/2001 | Douglas et al. |
| 6,246,966 B1 | 6/2001 | Perry |
| 6,251,083 B1 | 6/2001 | Yum et al. |
| 6,251,260 B1 | 6/2001 | Heller et al. |
| 6,254,586 B1 | 7/2001 | Mann et al. |
| 6,255,061 B1 | 7/2001 | Mori et al. |
| 6,256,533 B1 | 7/2001 | Yuzhakov et al. |
| 6,268,162 B1 | 7/2001 | Phillips et al. |
| 6,271,045 B1 | 8/2001 | Douglas et al. |
| 6,272,364 B1 | 8/2001 | Kurnik |
| 6,283,926 B1 | 9/2001 | Cunningham et al. |
| 6,289,230 B1 | 9/2001 | Chaiken et al. |
| 6,298,254 B2 | 10/2001 | Tamada |
| 6,299,578 B1 | 10/2001 | Kurnik et al. |
| 6,299,757 B1 | 10/2001 | Feldman et al. |
| 6,306,104 B1 | 10/2001 | Cunningham et al. |
| D450,711 S | 11/2001 | Istvan et al. |
| 6,312,612 B1 | 11/2001 | Sherman et al. |
| 6,312,812 B1 | 11/2001 | Hauser et al. |
| 6,312,888 B1 | 11/2001 | Wong et al. |
| 6,315,738 B1 | 11/2001 | Nishikawa et al. |
| 6,322,808 B1 | 11/2001 | Trautman et al. |

(56) References Cited

U.S. PATENT DOCUMENTS

| | | |
|---|---|---|
| 6,329,161 B1 | 12/2001 | Heller et al. |
| 6,331,266 B1 | 12/2001 | Powell et al. |
| 6,332,871 B1 | 12/2001 | Douglas et al. |
| 6,334,856 B1 | 1/2002 | Allen et al. |
| 6,350,273 B1 | 2/2002 | Minagawa et al. |
| 6,352,514 B1 | 3/2002 | Douglas et al. |
| 6,356,776 B1 | 3/2002 | Berner et al. |
| 6,358,265 B1 | 3/2002 | Thorne, Jr. et al. |
| 6,364,890 B1 | 4/2002 | Lum et al. |
| 6,375,626 B1 | 4/2002 | Allen et al. |
| 6,375,627 B1 | 4/2002 | Mauze et al. |
| 6,379,969 B1 | 4/2002 | Mauze et al. |
| 6,391,005 B1 | 5/2002 | Lum et al. |
| 6,391,645 B1 | 5/2002 | Huang et al. |
| 6,402,704 B1 | 6/2002 | McMorrow |
| 6,409,679 B2 | 6/2002 | Pyo |
| 6,428,664 B1 | 8/2002 | Bhullar et al. |
| 6,449,608 B1 | 9/2002 | Morita et al. |
| 6,455,324 B1 | 9/2002 | Douglas |
| 6,493,069 B1 | 12/2002 | Nagashimada et al. |
| 6,500,134 B1 | 12/2002 | Cassone |
| 6,520,973 B1 | 2/2003 | McGarry |
| 6,530,892 B1 | 3/2003 | Kelly |
| 6,537,243 B1 | 3/2003 | Henning et al. |
| 6,540,675 B2 | 4/2003 | Aceti et al. |
| 6,544,193 B2 | 4/2003 | Abreu |
| 6,544,475 B1 | 4/2003 | Douglas et al. |
| 6,549,796 B2 | 4/2003 | Sohrab |
| 6,555,061 B1 | 4/2003 | Leong et al. |
| 6,558,624 B1 | 5/2003 | Lemmon et al. |
| 6,579,690 B1 | 6/2003 | Bonnecaze et al. |
| 6,589,260 B1 | 7/2003 | Schmelzeisen-Redeker et al. |
| 6,591,124 B2 | 7/2003 | Sherman et al. |
| 6,591,125 B1 | 7/2003 | Buse et al. |
| 6,602,205 B1 | 8/2003 | Erickson et al. |
| 6,612,111 B1 | 9/2003 | Hodges et al. |
| 6,616,616 B2 | 9/2003 | Fritz et al. |
| 6,626,874 B1 | 9/2003 | Duchamp |
| 6,656,167 B2 | 12/2003 | Numao et al. |
| 6,662,031 B1 | 12/2003 | Khalil et al. |
| 6,679,852 B1 | 1/2004 | Schmelzeisen-Redeker et al. |
| 6,690,467 B1 | 2/2004 | Reel |
| 6,706,000 B2 | 3/2004 | Perez et al. |
| 6,706,049 B2 | 3/2004 | Moerman |
| 6,706,159 B2 | 3/2004 | Moerman et al. |
| 6,707,554 B1 | 3/2004 | Miltner et al. |
| 6,740,800 B1 | 5/2004 | Cunningham |
| 6,743,635 B2 | 6/2004 | Neel et al. |
| 6,744,502 B2 | 6/2004 | Hoff et al. |
| 6,748,275 B2 | 6/2004 | Lattner et al. |
| 6,753,187 B2 | 6/2004 | Cizdziel et al. |
| 6,766,817 B2 | 7/2004 | Da Silva |
| 6,775,001 B2 | 8/2004 | Friberg et al. |
| 6,793,633 B2 | 9/2004 | Douglas et al. |
| 6,830,669 B2 | 12/2004 | Miyazaki et al. |
| 6,836,678 B2 | 12/2004 | Tu |
| 6,837,858 B2 | 1/2005 | Cunningham et al. |
| 6,847,451 B2 | 1/2005 | Pugh |
| 6,849,052 B2 | 2/2005 | Uchigaki et al. |
| 6,890,421 B2 | 5/2005 | Ohara et al. |
| 6,896,850 B2 | 5/2005 | Subramanian et al. |
| 6,903,815 B2 | 6/2005 | Uchiyama et al. |
| 6,918,404 B2 | 7/2005 | Dias da Silva |
| 6,919,960 B2 | 7/2005 | Hansen et al. |
| 6,923,764 B2 | 8/2005 | Aceti et al. |
| 6,936,476 B1 | 8/2005 | Anderson et al. |
| D511,214 S | 11/2005 | Sasano et al. |
| 6,988,996 B2 | 1/2006 | Roe et al. |
| 7,004,928 B2 | 2/2006 | Aceti et al. |
| 7,011,630 B2 | 3/2006 | Desai et al. |
| 7,025,774 B2 | 4/2006 | Freeman et al. |
| D519,868 S | 5/2006 | Sasano et al. |
| 7,052,652 B2 | 5/2006 | Zanzucchi et al. |
| 7,066,586 B2 | 6/2006 | Da Silva |
| 7,066,890 B1 | 6/2006 | Lam et al. |
| 7,141,058 B2 | 11/2006 | Briggs et al. |
| 7,154,592 B2 | 12/2006 | Reynolds et al. |
| 7,156,809 B2 | 1/2007 | Quy |
| 7,163,616 B2 | 1/2007 | Vreeke et al. |
| 7,183,552 B2 | 2/2007 | Russell |
| 7,192,061 B2 | 3/2007 | Martin |
| 7,192,405 B2 | 3/2007 | DeNuzzio et al. |
| D540,343 S | 4/2007 | Cummins |
| 7,223,365 B2 | 5/2007 | Freiherr Von Der Goltz |
| 7,225,008 B1 | 5/2007 | Ward et al. |
| 7,226,461 B2 | 6/2007 | Boecker et al. |
| 7,229,458 B2 | 6/2007 | Boecker et al. |
| 7,258,673 B2 | 8/2007 | Racchini et al. |
| D551,243 S | 9/2007 | Young |
| 7,270,970 B2 | 9/2007 | Anderson et al. |
| 7,297,151 B2 | 11/2007 | Boecker et al. |
| 7,299,081 B2 | 11/2007 | Mace et al. |
| 7,316,700 B2 | 1/2008 | Alden et al. |
| 7,323,141 B2 | 1/2008 | Kirchhevel et al. |
| 7,323,315 B2 | 1/2008 | Marfurt |
| 7,341,830 B2 | 3/2008 | Horn et al. |
| 7,343,188 B2 | 3/2008 | Sohrab |
| 7,344,507 B2 | 3/2008 | Briggs et al. |
| 7,377,904 B2 | 5/2008 | Conway et al. |
| 7,379,167 B2 | 5/2008 | Mawhirt et al. |
| 7,427,377 B2 | 9/2008 | Zanzucchi et al. |
| 7,439,033 B2 | 10/2008 | Marfurt |
| D580,068 S | 11/2008 | Shigesada et al. |
| D580,558 S | 11/2008 | Shigesada et al. |
| 7,501,053 B2 | 3/2009 | Karinka et al. |
| 7,537,571 B2 | 5/2009 | Freeman et al. |
| D599,373 S | 9/2009 | Kobayashi et al. |
| D601,257 S | 9/2009 | Berlinger et al. |
| 7,582,063 B2 | 9/2009 | Wurster et al. |
| 7,585,278 B2 | 9/2009 | Aceti et al. |
| D601,444 S | 10/2009 | Jones et al. |
| D601,578 S | 10/2009 | Poulet et al. |
| 7,655,019 B2 | 2/2010 | LeVaughn et al. |
| 7,682,318 B2 | 3/2010 | Alden et al. |
| 7,708,701 B2 | 5/2010 | Boecker et al. |
| 7,713,214 B2 | 5/2010 | Freeman et al. |
| 7,725,149 B2 | 5/2010 | Peyser et al. |
| D622,393 S | 8/2010 | Gatrall et al. |
| 7,780,631 B2 | 8/2010 | Lum et al. |
| 7,803,123 B2 | 9/2010 | Perez et al. |
| 7,819,822 B2 | 10/2010 | Calasso et al. |
| 7,841,992 B2 | 11/2010 | Freeman et al. |
| 7,850,621 B2 | 12/2010 | Briggs et al. |
| 7,879,058 B2 | 2/2011 | Ikeda |
| 7,883,473 B2 | 2/2011 | LeVaughn et al. |
| 7,887,494 B2 | 2/2011 | Emery et al. |
| 7,892,183 B2 | 2/2011 | Boecker et al. |
| 7,955,492 B2 | 6/2011 | Fujiwara et al. |
| 7,959,583 B2 | 6/2011 | DeNuzzio et al. |
| 7,964,372 B2 | 6/2011 | Marfurt |
| D642,191 S | 7/2011 | Barnett et al. |
| 7,972,861 B2 | 7/2011 | Deng et al. |
| 7,988,644 B2 | 8/2011 | Freeman et al. |
| 8,012,103 B2 | 9/2011 | Escutia et al. |
| 8,012,104 B2 | 9/2011 | Escutia et al. |
| 8,105,849 B2 | 1/2012 | McDevitt et al. |
| D654,926 S | 2/2012 | Lipman et al. |
| 8,173,439 B2 | 5/2012 | Petrich et al. |
| 8,184,273 B2 | 5/2012 | Dosmann et al. |
| 8,202,231 B2 | 6/2012 | Freeman et al. |
| 8,231,832 B2 | 7/2012 | Zanzucchi et al. |
| 8,251,920 B2 | 8/2012 | Vreeke et al. |
| 8,262,614 B2 | 9/2012 | Freeman et al. |
| 8,267,870 B2 | 9/2012 | Freeman et al. |
| 8,280,476 B2 | 10/2012 | Jina |
| 8,298,255 B2 | 10/2012 | Conway et al. |
| 8,303,518 B2 | 11/2012 | Aceti et al. |
| 8,360,993 B2 | 1/2013 | Escutia et al. |
| 8,360,994 B2 | 1/2013 | Escutia et al. |
| 8,372,015 B2 | 2/2013 | Escutia et al. |
| 8,372,016 B2 | 2/2013 | Freeman et al. |
| 8,376,959 B2 | 2/2013 | Deck |
| 8,382,680 B2 | 2/2013 | Kistner et al. |
| 8,382,681 B2 | 2/2013 | Escutia et al. |

(56) References Cited

U.S. PATENT DOCUMENTS

| | | |
|---|---|---|
| 8,391,940 B2 | 3/2013 | Matzinger et al. |
| 8,419,657 B2 | 4/2013 | Roe |
| D691,174 S | 10/2013 | Lipman et al. |
| 8,574,168 B2 | 11/2013 | Freeman et al. |
| 8,574,895 B2 | 11/2013 | Freeman et al. |
| 8,696,880 B2 | 4/2014 | Beer et al. |
| 8,702,624 B1 | 4/2014 | Alden |
| 8,795,201 B2 | 8/2014 | Escutia et al. |
| 8,801,631 B2 | 8/2014 | Escutia et al. |
| 8,919,605 B2 | 12/2014 | Lipman et al. |
| 8,920,455 B2 | 12/2014 | Roe |
| 8,969,097 B2 | 3/2015 | Emery et al. |
| 9,017,356 B2 | 4/2015 | Schraga et al. |
| 9,034,639 B2 | 5/2015 | Freeman et al. |
| 9,060,723 B2 | 6/2015 | Escutia et al. |
| 9,060,727 B2 | 6/2015 | Saikley et al. |
| 9,063,102 B2 | 6/2015 | Hoenes et al. |
| 9,089,678 B2 | 7/2015 | Freeman et al. |
| 9,095,292 B2 | 8/2015 | Zanzucchi et al. |
| 9,095,847 B2 | 8/2015 | Porsch et al. |
| 9,097,679 B2 | 8/2015 | List et al. |
| 9,101,302 B2 | 8/2015 | Mace et al. |
| 9,131,886 B2 | 9/2015 | Harttig et al. |
| 9,138,179 B2 | 9/2015 | Hoenes et al. |
| 9,149,215 B2 | 10/2015 | Werner et al. |
| 9,173,608 B2 | 11/2015 | Kuhr et al. |
| 9,179,872 B2 | 11/2015 | Roe et al. |
| 9,186,097 B2 | 11/2015 | Frey et al. |
| 9,186,104 B2 | 11/2015 | Kraemer et al. |
| 9,186,468 B2 | 11/2015 | Freeman |
| 9,226,704 B2 | 1/2016 | Deck |
| 9,301,171 B2 | 3/2016 | Mattisson et al. |
| 9,314,194 B2 | 4/2016 | Deshmukh et al. |
| 9,326,718 B2 | 5/2016 | Petrich et al. |
| 9,332,931 B2 | 5/2016 | Chan |
| 9,332,932 B2 | 5/2016 | Okuyama et al. |
| 9,339,612 B2 | 5/2016 | Freeman et al. |
| 9,351,680 B2 | 5/2016 | Boecker |
| 9,364,172 B2 | 6/2016 | Konya et al. |
| 9,366,636 B2 | 6/2016 | Emery et al. |
| 9,375,169 B2 | 6/2016 | Choi et al. |
| 9,375,174 B2 | 6/2016 | Richter et al. |
| 9,375,177 B2 | 6/2016 | Planman et al. |
| 9,380,963 B2 | 7/2016 | Gofman et al. |
| 9,380,974 B2 | 7/2016 | Litherland et al. |
| 9,386,944 B2 | 7/2016 | Freeman et al. |
| 9,392,968 B2 | 7/2016 | Schraga |
| 9,439,591 B2 | 9/2016 | Frey et al. |
| 9,463,463 B2 | 10/2016 | He et al. |
| 9,480,419 B2 | 11/2016 | Weiss et al. |
| 9,480,420 B2 | 11/2016 | Konya et al. |
| 9,486,164 B2 | 11/2016 | Roe |
| 9,488,585 B2 | 11/2016 | Emeric et al. |
| 9,517,027 B2 | 12/2016 | Kan et al. |
| 9,560,993 B2 | 2/2017 | Freeman |
| 9,561,000 B2 | 2/2017 | Lum |
| 9,573,761 B2 | 2/2017 | List |
| 9,599,552 B2 | 3/2017 | Baldus et al. |
| 9,603,562 B2 | 3/2017 | Aceti et al. |
| 9,636,051 B2 | 5/2017 | Emery et al. |
| 9,668,687 B2 | 6/2017 | Volkmuth et al. |
| 9,671,387 B2 | 6/2017 | Thoes et al. |
| 9,717,452 B2 | 8/2017 | Roe et al. |
| 9,724,021 B2 | 8/2017 | Freeman et al. |
| 9,730,625 B2 | 8/2017 | Krasnow et al. |
| 9,782,114 B2 | 10/2017 | Reynolds et al. |
| 9,795,334 B2 | 10/2017 | Freeman et al. |
| 9,820,684 B2 | 11/2017 | Freeman et al. |
| 9,833,183 B2 | 12/2017 | Escutia et al. |
| 9,839,384 B2 | 12/2017 | Escutia et al. |
| 9,877,676 B2 | 1/2018 | Konya et al. |
| 9,880,254 B2 | 1/2018 | Richter et al. |
| 9,883,828 B2 | 2/2018 | Haar et al. |
| 9,897,610 B2 | 2/2018 | Lipman et al. |
| 9,927,386 B2 | 3/2018 | Wang et al. |
| 9,931,478 B2 | 4/2018 | Hirshberg |
| 9,939,403 B2 | 4/2018 | Richter et al. |
| 9,939,404 B2 | 4/2018 | Shimizu et al. |
| 9,943,256 B2 | 4/2018 | Varsavsky et al. |
| 9,943,259 B2 | 4/2018 | Kuhr et al. |
| 9,949,679 B2 | 4/2018 | Renlund |
| 9,965,587 B2 | 5/2018 | Aykroyd et al. |
| 9,968,284 B2 | 5/2018 | Vidalis et al. |
| 9,974,471 B1 | 5/2018 | Kam et al. |
| 9,983,140 B2 | 5/2018 | Dickopf |
| 9,987,427 B1 | 6/2018 | Polsky et al. |
| 10,034,628 B2 | 7/2018 | Freeman et al. |
| 10,080,517 B2 | 9/2018 | Chen et al. |
| 10,194,838 B2 | 2/2019 | Weiss et al. |
| 10,226,208 B2 | 3/2019 | Emery et al. |
| 10,278,621 B2 | 5/2019 | List |
| 10,309,905 B2 | 6/2019 | Dickopf |
| 10,327,689 B2 | 6/2019 | Krasnow et al. |
| 10,330,667 B2 | 6/2019 | Lipman et al. |
| 10,383,556 B2 | 8/2019 | Lipman et al. |
| 10,429,337 B2 | 10/2019 | Malecha et al. |
| 10,433,780 B2 | 10/2019 | Escutia et al. |
| 10,441,205 B2 | 10/2019 | Litherland et al. |
| 10,729,386 B2 | 8/2020 | Lipman et al. |
| 10,772,550 B2 | 9/2020 | Aceti et al. |
| 10,842,427 B2 | 11/2020 | Escutia et al. |
| 11,002,743 B2 | 5/2021 | Lipman et al. |
| 11,045,125 B2 | 6/2021 | Escutia et al. |
| 11,051,734 B2 | 7/2021 | Escutia et al. |
| 11,382,544 B2 | 7/2022 | Reynolds et al. |
| 11,399,744 B2 | 8/2022 | Emery et al. |
| 11,419,532 B2 | 8/2022 | Emery et al. |
| 11,553,860 B2 | 1/2023 | Lipman et al. |
| 11,672,452 B2 | 6/2023 | Escutia et al. |
| 2001/0001034 A1 | 5/2001 | Douglas |
| 2001/0027277 A1 | 10/2001 | Klitmose |
| 2001/0027328 A1 | 10/2001 | Lum et al. |
| 2001/0053891 A1 | 12/2001 | Ackley |
| 2002/0002326 A1 | 1/2002 | Causey, III et al. |
| 2002/0002344 A1 | 1/2002 | Douglas et al. |
| 2002/0004640 A1 | 1/2002 | Conn et al. |
| 2002/0006355 A1 | 1/2002 | Whitson |
| 2002/0016568 A1 | 2/2002 | Lebel et al. |
| 2002/0020688 A1 | 2/2002 | Sherman et al. |
| 2002/0022934 A1 | 2/2002 | Vogel et al. |
| 2002/0023852 A1 | 2/2002 | McIvor et al. |
| 2002/0042594 A1 | 4/2002 | Lum et al. |
| 2002/0045243 A1 | 4/2002 | Laska et al. |
| 2002/0052618 A1 | 5/2002 | Haar et al. |
| 2002/0067481 A1 | 6/2002 | Wolf et al. |
| 2002/0087056 A1 | 7/2002 | Aceti et al. |
| 2002/0136667 A1 | 9/2002 | Subramanian et al. |
| 2002/0137998 A1 | 9/2002 | Smart et al. |
| 2002/0160520 A1 | 10/2002 | Orloff et al. |
| 2002/0168290 A1 | 11/2002 | Yuzhakov et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0177764 A1 | 11/2002 | Sohrab |
| 2002/0183102 A1 | 12/2002 | Withers et al. |
| 2002/0188223 A1 | 12/2002 | Perez et al. |
| 2002/0198444 A1 | 12/2002 | Uchigaki et al. |
| 2003/0012693 A1 | 1/2003 | Otillar et al. |
| 2003/0028087 A1 | 2/2003 | Yuzhakov et al. |
| 2003/0028125 A1 | 2/2003 | Yuzhakov et al. |
| 2003/0039587 A1 | 2/2003 | Niermann |
| 2003/0060730 A1 | 3/2003 | Perez |
| 2003/0083685 A1 | 5/2003 | Freeman et al. |
| 2003/0083686 A1 | 5/2003 | Freeman et al. |
| 2003/0105961 A1 | 6/2003 | Zatloukal et al. |
| 2003/0116596 A1 | 6/2003 | Terasawa |
| 2003/0135166 A1 | 7/2003 | Gonnelli |
| 2003/0135333 A1 | 7/2003 | Aceti et al. |
| 2003/0143746 A1 | 7/2003 | Sage, Jr. |
| 2003/0153844 A1 | 8/2003 | Smith et al. |
| 2003/0153900 A1 | 8/2003 | Aceti et al. |
| 2003/0175987 A1 | 9/2003 | Verdonk et al. |
| 2003/0187395 A1 | 10/2003 | Gabel et al. |
| 2003/0206302 A1 | 11/2003 | Pugh |

(56) References Cited

U.S. PATENT DOCUMENTS

| | | |
|---|---|---|
| 2003/0207441 A1 | 11/2003 | Eyster et al. |
| 2003/0208113 A1 | 11/2003 | Mault et al. |
| 2003/0208140 A1 | 11/2003 | Pugh |
| 2003/0211617 A1 | 11/2003 | Jones |
| 2003/0211619 A1 | 11/2003 | Olson et al. |
| 2003/0212344 A1 | 11/2003 | Yuzhakov et al. |
| 2003/0212345 A1 | 11/2003 | McAllister et al. |
| 2003/0212347 A1 | 11/2003 | Sohrab |
| 2003/0216628 A1 | 11/2003 | Bortz et al. |
| 2004/0010207 A1 | 1/2004 | Flaherty et al. |
| 2004/0030353 A1 | 2/2004 | Schmelzeisen-Redeker et al. |
| 2004/0039303 A1 | 2/2004 | Wurster et al. |
| 2004/0049219 A1 | 3/2004 | Briggs et al. |
| 2004/0059256 A1 | 3/2004 | Perez |
| 2004/0072357 A1 | 4/2004 | Stiene et al. |
| 2004/0073140 A1 | 4/2004 | Douglas et al. |
| 2004/0092842 A1 | 5/2004 | Boecker et al. |
| 2004/0092995 A1 | 5/2004 | Boecker et al. |
| 2004/0094432 A1 | 5/2004 | Neel et al. |
| 2004/0096959 A1 | 5/2004 | Stiene et al. |
| 2004/0097796 A1 | 5/2004 | Berman et al. |
| 2004/0098009 A1 | 5/2004 | Boecker et al. |
| 2004/0102803 A1 | 5/2004 | Boecker et al. |
| 2004/0120848 A1 | 6/2004 | Teodorczyk |
| 2004/0122339 A1 | 6/2004 | Roe |
| 2004/0132167 A1 | 7/2004 | Rule et al. |
| 2004/0138588 A1 | 7/2004 | Saikley et al. |
| 2004/0155084 A1 | 8/2004 | Brown |
| 2004/0157339 A1 | 8/2004 | Burke et al. |
| 2004/0178218 A1 | 9/2004 | Schomakers et al. |
| 2004/0186394 A1 | 9/2004 | Roe et al. |
| 2004/0191119 A1 | 9/2004 | Zanzucchi et al. |
| 2004/0202576 A1 | 10/2004 | Aceti et al. |
| 2004/0230216 A1 | 11/2004 | Levaughn et al. |
| 2004/0236251 A1 | 11/2004 | Roe et al. |
| 2004/0238675 A1 | 12/2004 | Banaszkiewicz et al. |
| 2004/0242982 A1 | 12/2004 | Sakata et al. |
| 2004/0249253 A1 | 12/2004 | Racchini et al. |
| 2004/0259180 A1 | 12/2004 | Burke et al. |
| 2005/0004494 A1 | 1/2005 | Perez et al. |
| 2005/0010134 A1 | 1/2005 | Douglas et al. |
| 2005/0011759 A1 | 1/2005 | Moerman et al. |
| 2005/0015020 A1 | 1/2005 | LeVaughn et al. |
| 2005/0027182 A1 | 2/2005 | Siddiqui et al. |
| 2005/0033340 A1 | 2/2005 | Lipoma et al. |
| 2005/0038680 A1 | 2/2005 | McMahon |
| 2005/0070819 A1 | 3/2005 | Poux et al. |
| 2005/0096686 A1 | 5/2005 | Allen |
| 2005/0106713 A1 | 5/2005 | Phan et al. |
| 2005/0109386 A1 | 5/2005 | Marshall |
| 2005/0153428 A1 | 7/2005 | Matsumoto |
| 2005/0154410 A1 | 7/2005 | Conway et al. |
| 2005/0159656 A1 | 7/2005 | Hockersmith et al. |
| 2005/0159678 A1 | 7/2005 | Taniike et al. |
| 2005/0176133 A1 | 8/2005 | Miyashita et al. |
| 2005/0187532 A1 | 8/2005 | Thurau et al. |
| 2005/0192492 A1 | 9/2005 | Cho et al. |
| 2005/0202567 A1 | 9/2005 | Zanzucchi et al. |
| 2005/0202733 A1 | 9/2005 | Yoshimura et al. |
| 2005/0209518 A1 | 9/2005 | Sage, Jr. et al. |
| 2005/0215872 A1 | 9/2005 | Berner et al. |
| 2005/0215923 A1 | 9/2005 | Wiegel |
| 2005/0245844 A1 | 11/2005 | Mace et al. |
| 2005/0255001 A1 | 11/2005 | Padmanabhan et al. |
| 2005/0277972 A1 | 12/2005 | Wong et al. |
| 2006/0008389 A1 | 1/2006 | Sacherer et al. |
| 2006/0036134 A1 | 2/2006 | Tarassenko et al. |
| 2006/0052724 A1 | 3/2006 | Roe |
| 2006/0064035 A1 | 3/2006 | Wang et al. |
| 2006/0079809 A1 | 4/2006 | Goldberger et al. |
| 2006/0094985 A1 | 5/2006 | Aceti et al. |
| 2006/0117616 A1 | 6/2006 | Jones et al. |
| 2006/0122536 A1 | 6/2006 | Haar et al. |
| 2006/0135873 A1 | 6/2006 | Karo et al. |
| 2006/0155317 A1 | 7/2006 | List |
| 2006/0161078 A1 | 7/2006 | Schraga |
| 2006/0178600 A1 | 8/2006 | Kennedy et al. |
| 2006/0189908 A1 | 8/2006 | Kennedy |
| 2006/0200044 A1 | 9/2006 | Freeman et al. |
| 2006/0204399 A1 | 9/2006 | Freeman et al. |
| 2006/0224172 A1 | 10/2006 | LeVaughn et al. |
| 2006/0229533 A1 | 10/2006 | Hoenes et al. |
| 2006/0241517 A1 | 10/2006 | Fowler et al. |
| 2006/0257993 A1 | 11/2006 | McDevitt et al. |
| 2006/0259102 A1 | 11/2006 | Slatkine |
| 2006/0264996 A1 | 11/2006 | LeVaughn et al. |
| 2006/0281187 A1 | 12/2006 | Emery et al. |
| 2007/0016104 A1 | 1/2007 | Jansen et al. |
| 2007/0017824 A1 | 1/2007 | Rippeth et al. |
| 2007/0032250 A1* | 2/2007 | Feher .................... H04M 11/04 455/456.2 |
| 2007/0033074 A1 | 2/2007 | Nitzan et al. |
| 2007/0060842 A1 | 3/2007 | Alvarez-Icaza et al. |
| 2007/0078313 A1 | 4/2007 | Emery et al. |
| 2007/0078358 A1 | 4/2007 | Escutia et al. |
| 2007/0083130 A1 | 4/2007 | Thomson et al. |
| 2007/0083131 A1 | 4/2007 | Escutia et al. |
| 2007/0093786 A1 | 4/2007 | Goldsmith et al. |
| 2007/0100255 A1 | 5/2007 | Boecker et al. |
| 2007/0112281 A1 | 5/2007 | Olson |
| 2007/0179352 A1 | 8/2007 | Randlov et al. |
| 2007/0179404 A1 | 8/2007 | Escutia et al. |
| 2007/0179405 A1 | 8/2007 | Emery et al. |
| 2007/0253531 A1 | 11/2007 | Okuzawa et al. |
| 2007/0255181 A1 | 11/2007 | Alvarez-Icaza et al. |
| 2007/0255302 A1 | 11/2007 | Koeppel et al. |
| 2008/0004601 A1 | 1/2008 | Jennewine et al. |
| 2008/0012701 A1 | 1/2008 | Kass et al. |
| 2008/0046831 A1 | 2/2008 | Imai et al. |
| 2008/0064986 A1 | 3/2008 | Kraemer et al. |
| 2008/0064987 A1 | 3/2008 | Escutia et al. |
| 2008/0077048 A1 | 3/2008 | Escutia et al. |
| 2008/0119702 A1 | 5/2008 | Reggiardo |
| 2008/0139910 A1 | 6/2008 | Mastrototaro et al. |
| 2008/0194934 A1 | 8/2008 | Ray et al. |
| 2008/0200838 A1 | 8/2008 | Goldberger et al. |
| 2008/0206799 A1 | 8/2008 | Blomquist |
| 2008/0255598 A1 | 10/2008 | LeVaughn et al. |
| 2008/0268485 A1 | 10/2008 | Guarino et al. |
| 2008/0269625 A1 | 10/2008 | Halperin et al. |
| 2008/0274447 A1 | 11/2008 | Mecklenburg |
| 2009/0054810 A1 | 2/2009 | Zanzucchi et al. |
| 2009/0149717 A1 | 6/2009 | Brauer et al. |
| 2009/0149729 A1 | 6/2009 | Young et al. |
| 2009/0156923 A1 | 6/2009 | Power et al. |
| 2009/0292489 A1 | 11/2009 | Burke et al. |
| 2009/0301899 A1 | 12/2009 | Hodges et al. |
| 2010/0010374 A1 | 1/2010 | Escutia et al. |
| 2010/0021947 A1 | 1/2010 | Emery et al. |
| 2010/0021948 A1 | 1/2010 | Lipman et al. |
| 2010/0095229 A1 | 4/2010 | Dixon et al. |
| 2010/0152660 A1 | 6/2010 | Mack et al. |
| 2010/0174211 A1 | 7/2010 | Frey et al. |
| 2010/0185120 A1 | 7/2010 | Sacherer et al. |
| 2010/0217155 A1 | 8/2010 | Poux et al. |
| 2010/0249652 A1 | 9/2010 | Rush et al. |
| 2010/0256525 A1 | 10/2010 | List et al. |
| 2010/0331650 A1 | 12/2010 | Batman et al. |
| 2011/0082709 A1 | 4/2011 | Li et al. |
| 2011/0098599 A1 | 4/2011 | Emery et al. |
| 2011/0105872 A1 | 5/2011 | Chickering, III et al. |
| 2011/0118986 A1 | 5/2011 | Stewart et al. |
| 2011/0162978 A1 | 7/2011 | Cardosi et al. |
| 2011/0201909 A1 | 8/2011 | Emery et al. |
| 2011/0288440 A1 | 11/2011 | Escutia et al. |
| 2011/0288443 A1 | 11/2011 | Escutia et al. |
| 2011/0294152 A1 | 12/2011 | Lipman et al. |
| 2012/0166090 A1 | 6/2012 | Lipman et al. |
| 2012/0271197 A1 | 10/2012 | Castle et al. |
| 2012/0296179 A1 | 11/2012 | Zanzucchi et al. |
| 2013/0110516 A1 | 5/2013 | Abulhaj et al. |
| 2013/0144189 A1 | 6/2013 | Escutia et al. |
| 2013/0158430 A1 | 6/2013 | Aceti et al. |
| 2013/0158432 A1 | 6/2013 | Escutia et al. |

(56) References Cited

U.S. PATENT DOCUMENTS

| | | |
|---|---|---|
| 2013/0172698 A1 | 7/2013 | Reynolds et al. |
| 2013/0274568 A1 | 10/2013 | Escutia et al. |
| 2013/0274579 A1 | 10/2013 | Richter et al. |
| 2014/0012116 A1 | 1/2014 | Okuyama |
| 2014/0316301 A1 | 10/2014 | Escutia et al. |
| 2014/0336480 A1 | 11/2014 | Escutia et al. |
| 2014/0376762 A1 | 12/2014 | Lipman et al. |
| 2015/0037898 A1 | 2/2015 | Baldus et al. |
| 2015/0153351 A1 | 6/2015 | Lipman et al. |
| 2015/0182157 A1 | 7/2015 | Boriah et al. |
| 2015/0212006 A1 | 7/2015 | Emery et al. |
| 2015/0238131 A1 | 8/2015 | Richter et al. |
| 2015/0268228 A1 | 9/2015 | Schulat et al. |
| 2015/0335272 A1 | 11/2015 | Natale et al. |
| 2016/0011178 A1 | 1/2016 | Hoenes et al. |
| 2016/0038066 A1 | 2/2016 | Escutia et al. |
| 2016/0256106 A1 | 9/2016 | Krasnow et al. |
| 2016/0367178 A1 | 12/2016 | Emery et al. |
| 2016/0374603 A1 | 12/2016 | Shaanan et al. |
| 2017/0095188 A1 | 4/2017 | Emery et al. |
| 2017/0319121 A1 | 11/2017 | Aceti et al. |
| 2017/0354355 A1 | 12/2017 | Emery et al. |
| 2018/0008178 A1 | 1/2018 | Reynolds et al. |
| 2018/0214059 A1 | 8/2018 | Escutia et al. |
| 2018/0296143 A1 | 10/2018 | Anderson, III et al. |
| 2018/0310865 A1 | 11/2018 | Escutia et al. |
| 2018/0338713 A1 | 11/2018 | Polsky et al. |
| 2019/0000365 A1 | 1/2019 | Beyerlein et al. |
| 2019/0025318 A1 | 1/2019 | Lipman et al. |
| 2019/0104976 A1 | 4/2019 | Reynolds et al. |
| 2019/0175086 A1 | 6/2019 | Yang |
| 2019/0209064 A1 | 7/2019 | Emery et al. |
| 2019/0209820 A1 | 7/2019 | Chickering, III et al. |
| 2019/0269358 A1 | 9/2019 | Messerschmidt |
| 2019/0274607 A1 | 9/2019 | Krasnow et al. |
| 2019/0391129 A1 | 12/2019 | Lipman et al. |
| 2020/0155052 A1 | 5/2020 | Litherland et al. |
| 2020/0214605 A1 | 7/2020 | Lipman et al. |
| 2020/0237280 A1 | 7/2020 | Escutia et al. |
| 2021/0177361 A1 | 6/2021 | Lipman et al. |
| 2021/0307662 A1 | 10/2021 | Escutia et al. |
| 2021/0330225 A1 | 10/2021 | Escutia et al. |
| 2022/0026436 A1 | 1/2022 | Lipman et al. |
| 2022/0039711 A1 | 2/2022 | Escutia et al. |
| 2022/0322980 A1 | 10/2022 | Escutia et al. |
| 2023/0190144 A1 | 6/2023 | Emery et al. |

FOREIGN PATENT DOCUMENTS

| | | |
|---|---|---|
| CA | 2624117 A1 | 4/2007 |
| DE | 19705091 A1 | 2/1999 |
| DE | 19922413 A1 | 11/2000 |
| DE | 10302501 A1 | 8/2004 |
| EP | 0103426 A2 | 3/1984 |
| EP | 0255338 A2 | 2/1988 |
| EP | 0256806 A2 | 2/1988 |
| EP | 0160708 B1 | 10/1989 |
| EP | 0356418 A2 | 2/1990 |
| EP | 0396016 A2 | 11/1990 |
| EP | 0397424 A2 | 11/1990 |
| EP | 0409032 A2 | 1/1991 |
| EP | 0762311 A2 | 3/1997 |
| EP | 0849584 A2 | 6/1998 |
| EP | 0877250 A2 | 11/1998 |
| EP | 1037048 A2 | 9/2000 |
| EP | 1060768 A2 | 12/2000 |
| EP | 1118856 A1 | 7/2001 |
| EP | 1266607 A2 | 12/2002 |
| EP | 1360934 A1 | 11/2003 |
| EP | 1369688 A2 | 12/2003 |
| EP | 1486766 A1 | 12/2004 |
| EP | 1529489 A1 | 5/2005 |
| EP | 1769735 A1 | 4/2007 |
| EP | 1987766 A2 | 11/2008 |
| JP | S61290342 A | 12/1986 |
| JP | S63305841 A | 12/1988 |
| JP | H01318963 A | 12/1989 |
| JP | H0363570 A | 3/1991 |
| JP | H0393189 A | 4/1991 |
| JP | H0767861 A | 3/1995 |
| JP | H07213925 A | 8/1995 |
| JP | H09168530 A | 6/1997 |
| JP | H09266889 A | 10/1997 |
| JP | H09294737 A | 11/1997 |
| JP | H09313465 A | 12/1997 |
| JP | H1024028 A | 1/1998 |
| JP | H10505258 A | 5/1998 |
| JP | H10508518 A | 8/1998 |
| JP | H10318970 A | 12/1998 |
| JP | H1156822 A | 3/1999 |
| JP | H11281779 A | 10/1999 |
| JP | 2000116629 A | 4/2000 |
| JP | 2000126161 A | 5/2000 |
| JP | 2000168754 A | 6/2000 |
| JP | 2000254111 A | 9/2000 |
| JP | 2001159618 A | 6/2001 |
| JP | 2001281242 A | 10/2001 |
| JP | 2001305096 A | 10/2001 |
| JP | 2001330581 A | 11/2001 |
| JP | 2002502045 A | 1/2002 |
| JP | 2002085384 A | 3/2002 |
| JP | 2002514453 A | 5/2002 |
| JP | 2002168862 A | 6/2002 |
| JP | 2003507719 A | 2/2003 |
| JP | 2003108679 A | 4/2003 |
| JP | 2004000598 A | 1/2004 |
| JP | 2004500948 A | 1/2004 |
| JP | 2004117339 A | 4/2004 |
| JP | 2004202256 A | 7/2004 |
| JP | 2004209266 A | 7/2004 |
| JP | 2004519302 A | 7/2004 |
| JP | 2004522500 A | 7/2004 |
| JP | 2004528936 A | 9/2004 |
| JP | 2005503538 A | 2/2005 |
| JP | 2005506857 A | 3/2005 |
| JP | 3638958 B2 | 4/2005 |
| JP | 2005087613 A | 4/2005 |
| JP | 2005525149 A | 8/2005 |
| JP | 2005237938 A | 9/2005 |
| JP | 2005525846 A | 9/2005 |
| JP | 2005527254 A | 9/2005 |
| JP | 2006506185 A | 2/2006 |
| JP | 2006068384 A | 3/2006 |
| JP | 2006512969 A | 4/2006 |
| JP | 2006512974 A | 4/2006 |
| JP | 2006516723 A | 7/2006 |
| JP | 2006239062 A | 9/2006 |
| JP | 2006521555 A | 9/2006 |
| JP | 2006284481 A | 10/2006 |
| JP | 2006527013 A | 11/2006 |
| JP | 2007054407 A | 3/2007 |
| JP | 2007067698 A | 3/2007 |
| JP | 2007521031 A | 8/2007 |
| JP | 2007527287 A | 9/2007 |
| JP | 2007311196 A | 11/2007 |
| JP | 2007537804 A | 12/2007 |
| JP | 2008043741 A | 2/2008 |
| JP | 2008504893 A | 2/2008 |
| JP | 2008125813 A | 6/2008 |
| JP | 2008212324 A | 9/2008 |
| JP | 2009509645 A | 3/2009 |
| JP | 2009509667 A | 3/2009 |
| JP | 2009509679 A | 3/2009 |
| JP | 2010104491 A | 5/2010 |
| JP | 2012213477 A | 11/2012 |
| JP | 2013505747 A | 2/2013 |
| KR | 100458978 B1 | 5/2005 |
| WO | WO-8605966 A1 | 10/1986 |
| WO | WO-8800812 A1 | 2/1988 |
| WO | WO-8807666 A1 | 10/1988 |
| WO | WO-9114212 A1 | 9/1991 |
| WO | WO-9413203 A1 | 6/1994 |
| WO | WO-9510223 A2 | 4/1995 |
| WO | WO-9604857 A1 | 2/1996 |

(56) References Cited

FOREIGN PATENT DOCUMENTS

| | | |
|---|---|---|
| WO | WO-9607907 A1 | 3/1996 |
| WO | WO-9614026 A1 | 5/1996 |
| WO | WO-9625088 A1 | 8/1996 |
| WO | WO-9704707 A1 | 2/1997 |
| WO | WO-9715227 A1 | 5/1997 |
| WO | WO-9729847 A1 | 8/1997 |
| WO | WO-9730344 A1 | 8/1997 |
| WO | WO-9741421 A1 | 11/1997 |
| WO | WO-9742885 A1 | 11/1997 |
| WO | WO-9742888 A1 | 11/1997 |
| WO | WO-9743962 A1 | 11/1997 |
| WO | WO-9800193 A1 | 1/1998 |
| WO | WO-9831275 A1 | 7/1998 |
| WO | WO-9835225 A1 | 8/1998 |
| WO | WO-9912008 A1 | 3/1999 |
| WO | WO-9923492 A1 | 5/1999 |
| WO | WO-9944508 A1 | 9/1999 |
| WO | WO-9956954 A1 | 11/1999 |
| WO | WO-9958051 A1 | 11/1999 |
| WO | WO-9962576 A1 | 12/1999 |
| WO | WO-0009184 A1 | 2/2000 |
| WO | WO-0013573 A1 | 3/2000 |
| WO | WO-0014269 A1 | 3/2000 |
| WO | WO-0014535 A1 | 3/2000 |
| WO | WO-0018449 A2 | 4/2000 |
| WO | WO-0036400 A1 | 6/2000 |
| WO | WO-0042422 A1 | 7/2000 |
| WO | WO-0074763 A2 | 12/2000 |
| WO | WO-0078208 A1 | 12/2000 |
| WO | WO-0113795 A1 | 3/2001 |
| WO | WO-0116575 A1 | 3/2001 |
| WO | WO-0141643 A1 | 6/2001 |
| WO | WO-0152727 A1 | 7/2001 |
| WO | WO-0164105 A1 | 9/2001 |
| WO | WO-0172220 A1 | 10/2001 |
| WO | WO-0180728 A1 | 11/2001 |
| WO | WO-0185233 A2 | 11/2001 |
| WO | WO-0191634 A2 | 12/2001 |
| WO | WO-0200101 A2 | 1/2002 |
| WO | WO-0249507 A1 | 6/2002 |
| WO | WO-0249509 A1 | 6/2002 |
| WO | WO-02078533 A2 | 10/2002 |
| WO | WO-02082052 A2 | 10/2002 |
| WO | WO-02101359 A2 | 12/2002 |
| WO | WO-03007819 A1 | 1/2003 |
| WO | WO-03030984 A1 | 4/2003 |
| WO | WO-03066128 A2 | 8/2003 |
| WO | WO-03070099 A1 | 8/2003 |
| WO | WO-03071940 A1 | 9/2003 |
| WO | WO-03088834 A1 | 10/2003 |
| WO | WO-2004045375 A2 | 6/2004 |
| WO | WO-2004062499 A1 | 7/2004 |
| WO | WO-2004062500 A1 | 7/2004 |
| WO | WO-2004064636 A1 | 8/2004 |
| WO | WO-2004085995 A2 | 10/2004 |
| WO | WO-2004091693 A2 | 10/2004 |
| WO | WO-2004105827 A2 | 12/2004 |
| WO | WO-2004112612 A1 | 12/2004 |
| WO | WO-2005006939 A2 | 1/2005 |
| WO | WO-2005009238 A1 | 2/2005 |
| WO | WO-2005013824 A1 | 2/2005 |
| WO | WO-2005018709 A2 | 3/2005 |
| WO | WO-2005018710 A2 | 3/2005 |
| WO | WO-2005054840 A1 | 6/2005 |
| WO | WO-2005084543 A1 | 9/2005 |
| WO | WO-2005084546 A2 | 9/2005 |
| WO | WO-2005085995 A1 | 9/2005 |
| WO | WO-2005112763 A1 | 12/2005 |
| WO | WO-2006004859 A2 | 1/2006 |
| WO | WO-2006031920 A2 | 3/2006 |
| WO | WO-2006138226 A2 | 12/2006 |
| WO | WO-2007041062 A2 | 4/2007 |
| WO | WO-2007041063 A2 | 4/2007 |
| WO | WO-2007041244 A2 | 4/2007 |
| WO | WO-2007041287 A2 | 4/2007 |
| WO | WO-2007041355 A2 | 4/2007 |
| WO | WO-2007054317 A1 | 5/2007 |
| WO | WO-2007088875 A1 | 8/2007 |
| WO | WO-2007108519 A1 | 9/2007 |
| WO | WO-2007112034 A2 | 10/2007 |
| WO | WO-2007131036 A1 | 11/2007 |
| WO | WO-2008027319 A2 | 3/2008 |
| WO | WO-2008062648 A1 | 5/2008 |
| WO | WO-2009145920 A1 | 12/2009 |
| WO | WO-2009148624 A1 | 12/2009 |
| WO | WO-2009148626 A1 | 12/2009 |
| WO | WO-2011065981 A1 | 6/2011 |
| WO | WO-2011162823 A1 | 12/2011 |
| WO | WO-2012127870 A1 | 9/2012 |
| WO | WO-2013020103 A1 | 2/2013 |
| WO | WO-2013104676 A1 | 7/2013 |
| WO | WO-2014205412 A1 | 12/2014 |
| WO | WO-2018191700 A1 | 10/2018 |

OTHER PUBLICATIONS

ADA (Jan. 1994). "Self-Monitoring of Blood Glucose," Consensus Statement Diabetes Care 17(1):81-86.
Anonymous. (Jun. 23, 1998). Taking the "Ouch" Out of Needles: Arrays of "Microneedles" Offer New Techniques for Drug Delivery, Science Daily, located at http:www.sciencedaily.com/releases/1998/06/980623045850.htm, last visited Jan. 14, 3 pages.
Beregszaszi, M. et al. (Jul. 1997). "Nocturnal Hypoglycemia in Children and Adolescents with Insulin-Dependent Diabetes Mellitus: Prevalence and Risk Factors," J. Pediatrics 131 (1 Pt. 1):27-33.
Brazzle, J. et al. Active Microneedles with Integrated Functionality, Solid-State Sensor and Actuator Workshop, Hilton Head Island, South Carolina, Jun. 4-8, 2000, Technical Digest, 199-202.
Burge, M.R., (Aug. 2001). "Lack of Compliance with Home Blood Glucose Monitoring Predicts Hospitalization in Diabetes", Diabetes Care 24(8): 1502-1503.
Chase, H.P. et al. (Feb. 2001). "Continuous Subcutaneous Glucose Monitoring in Children with Type 1 Diabetes," Pediatrics 10 7(2):222-226.
Clarke, W.L. et al. (Sep.-Oct. 1981). "Evaluation of a New Reflectance Photometer for Use in Home Blood Glucose Monitoring," Diabetes Care, 4(5):547-550.
Clarke, W.L. et al. (Sep.-Oct. 1987). "Evaluating Clinical Accuracy of Systems for Self-Monitoring of Blood Glucose," Diabetes Care 1 0(5):622-628.
Collison, M.E. et al. (Sep. 1999). "Analytical Characterization of Electrochemical Biosensor Test Strips for Measurement of Glucose in Low-Volume Interstitial Fluid Samples," Clinical Chemistry 45(9):1665-1673.
Coster, S. et al. (2000). "Monitoring Blood Glucose Control in Diabetes Mellitus: A Systematic Review." Health Technology Assessment 4(12):1-93.
Cox, D.J. et al. (Jun. 1997). "Understanding Error Grid Analysis," Diabetes Care 20(6):911-912.
D'Arrigo, T.D. (Mar. 2000). "GlucoWatch Monitor Poised for Approval," Diabetes Forecast, 53(3):43-44.
European Office Action dated Oct. 26, 2015, for EP Patent Application 12820723.0, filed on Aug. 3, 2012. 4 pages. (1.42).
European Search Report and Opinion issued in European Patent Application No. 21209547 dated Mar. 18, 2022, 8 pgs.
Examination Report dated Nov. 8, 2022, issued in European Patent Application No. 14813126.1, 6 pgs.
Extended European Search Report dated Feb. 28, 2022, by the European Patent Office for Patent Application No. 21153320.3, filed Jun. 8, 2009, 12 pages.
Extended European Search Report dated Aug. 27, 2012, for European Patent Application No. 09 758 789.3, filed on Jun. 8, 2009, 13 pages.
Extended European Search Report dated Aug. 8, 2022, for EP Application No. 22153909.1, 10 pages.
Extended European Search Report dated Feb. 26, 2020, for European Application No. 19196465.9, filed on Jun. 8, 2009, 6 pages.
Extended European Search Report dated Jan. 20, 2017, for EP Application No. 14813126.1, filed Jun. 20, 2014, 8 pages.

(56) References Cited

OTHER PUBLICATIONS

Extended European Search Report dated Jan. 22, 2015, for EP Patent Application 12820723.0, filed on Aug. 3, 2012, 4 pages.
Extended European Search Report dated Jun. 16, 2014, for EP Application No. 09758787.7, filed on Jun. 8, 2009, 6 pages.
Extended European Search Report dated May 8, 2015, for EP Application No. 12 842 020.5, filed on Aug. 31, 2012, 7 pages.
Extended European Search Report dated Nov. 10, 2020, for European Application No. 20169957.6, filed on Aug. 3, 2012, 9 pages.
Extended European Search Report dated Oct. 27, 2016, for EP Application No. 11 798 518.4, filed on Jun. 24, 2011, 8 pages.
Extended European Search Report dated Oct. 30, 2018, for EP Patent Application 18166131.5, filed on Aug. 3, 2012. 8 pages.
Extended European Search Report dated Nov. 8, 2016 from the European Patent Office for Application No. 16167087.2, filed Aug. 3, 2012, 6 pages.
Feldman, B. et al. (2000). "FreeStyle™: A Small-Volume Electrochemical Glucose Sensor for Home Blood Glucose Testing," Diabetes Technology and Therapeutics, 2(2):221-229.
Final Office Action issued in U.S. Appl. No. 13/566,886, dated Jan. 20, 2016, 11 pages.
Final Office Action dated Nov. 1, 2010, for U.S. Appl. No. 11/311,667, filed Dec. 20, 2005, 10 pages.
Final Office Action dated Nov. 21, 2011, for U.S. Appl. No. 11/311,667, filed Dec. 20, 2005, 8 pages.
Final Office Action dated Apr. 25, 2019, for U.S. Appl. No. 14/311,114, filed Jun. 20, 2014, 16 pages.
Final Office Action dated Apr. 30, 2013, for U.S. Appl. No. 13/168,644, filed Jun. 24, 2011, 10 pages. (21.00).
Final Office Action dated Aug. 12, 2016, for U.S. Appl. No. 13/168,644, filed Jun. 24, 2011, 18 pages.—(21.00).
Final Office Action dated Dec. 26, 2014, for U.S. Appl. No. 12/457,331, filed Jun. 8, 2009, 10 pages.
Final Office Action dated Jan. 21, 2011, for U.S. Appl. No. 11/529,613, filed Sep. 29, 2006, 7 pages.
Final Office Action dated Jul. 9, 2008, for U.S. Appl. No. 11/529,613, filed Sep. 29, 2006, 20 pages.
Final Office Action dated Jun. 12, 2018, for U.S. Appl. No. 15/499,821, filed Apr. 27, 2017, 13 pages.
Final Office Action dated Jun. 14, 2021, for U.S. Appl. No. 15/499,821, filed Apr. 27, 2017, 14 pages.
Final Office Action dated May 5, 2016 for U.S. Appl. No. 12/457,331, filed Jun. 8, 2009, 11 pages.
Final Office Action dated May 5, 2016, for U.S. Appl. No. 14/311,114, filed Jun. 20, 2014, 13 pages.—(24.00).
Final Office Action dated May 8, 2012, for U.S. Appl. No. 12/457,331, filed Jun. 8, 2009, 7 pages.
Final Office Action dated Nov. 13, 2017, for U.S. Appl. No. 14/311,114, filed Jun. 20, 2014, 15 pages.
Final Office Action dated Nov. 23, 2009, for U.S. Appl. No. 11/529,613, filed Sep. 29, 2006, 20 pages.
Hemmerich, K.J. et al. (Apr. 1995)."Guide to Engineering Thermoplastics," Medical Devices and Diagnostic Industry pp. 39-59.
Integ. (2000). "LifeGuideO Glucose Meter. No Lancets. No Blood," located at<http://www.integonline.com>, last visited May 1, 2000, 10 pages.
International Search Report dated Jul. 28, 2009, for PCT Application No. PCT/US2009/003445, filed on Jun. 8, 2009, 2 pages.
International Search Report dated Nov. 14, 2011, for PCT Application No. PCT/US2011/001132, filed on Jun. 24, 2011, 2 pages. (21.40).
International Search Report dated Oct. 15, 2014 for PCT Application No. PCT/US2014/043516, filed on Jun. 20, 2014, 2 pages. (24.40).
International Search Report dated Oct. 19, 2012 for PCT Application No. PCT/US2012/049629, filed on Aug. 3, 2012, 3 pages.
Ishii H. et al., (Aug. 2001). "Seasonal Variation of Glycemic Control in Type 2 Diabetic Patients", Diabetes Care 24(8): 1503.
Johnson, R.N. et al. (2001). "Error Detection and Measurement in Glucose Monitors," Clinica Chimica Acta 307:61-67.
Johnson, R.N. et al. (Jan. 1998). "Accuracy of Devices Used for Self-Monitoring of Blood Glucose," Annals of Clinical Biochemistry 35(1 ):68-74.
Johnson, R.N. et al. (Jan. 1999). "Analytical Error of Home Glucose Monitors: A Comparison of 18 Systems," Annals of Clinical Biochemistry 36(1) :72-79.
Khalil, "Non-invasive glucose measurement technologies: an update from 1999 to the dawn of the new millennium," Diabetes Technology & Therapeutics., vol. 6, No. 5, 2004, pp. 690-696.
Kumetrix, Inc. (Dec. 1999). "Painless Blood Glucose Monitoring, Courtesy of the Mosquito," Start-Up pp. 27-28.
Lee, S-C. (Jun. 1999). "Light Scattering by Closely Spaced Parallel Cylinders Embedded in a Finite Dielectric Slab," Journal of the Optical Society of America A 16(6):1350-1361.
Mahler, R.J. et al. (1999). "Clinical Review 102, Type 2 Diabetes Mellitus: Update on Diagnosis Pathophysiology, and Treatment," The Journal of Clinical Endocrinology and Metabolism 84(4):1165-1171.
Massey V. et al. (Aug. 1960). "Studies on the Reaction Mechanism of Lipoyl Dehydrogenase" Biochim. Biophys. Acta 48: 33-47.
McGarraugh, G. et al. (2001). "Physiological Influences on Off-Finger Glucose Testing," Diabetes Technology & Therapeutics 3(3):367-376.
McNichols, R.J. et al. (Jan. 2000). "Optical Glucose Sensing in Biological Fluids: An Overview," Journal of Biomedical Optics, 5(1):5-16.
Medline Plus. (Jun. 17, 2008), Medical Encyclopedia, Monitor Blood Glucose—Series: Part 1-4, 6 pages.
Nathan, et al., Diabetes Control and Complications Trial Research Group, "The Effect of Intensive Treatment of Diabetes on the Development and Progression of Long-Term Complications in Insulin-Dependent Diabetes Mellitus." The New England Journal of Medicine, Sep. 30, 1993, 977-986.
Neeley, WE. (1983). "Multilayer Film Analysis for Glucose in 1-I-LL Samples of Plasma," Clinical Chemistry 29(12):2103-2105.
Neeley, W.E. (1983). "Reflectance Digital Matrix Photometry," Clinical Chemistry 29(6):1038-1041.
Neeley, W.E. (1988). "A Reflectance Photometer with a Square Photodiode Array Detector for Use on Multilayer Dry-Film Slides," Clinical Chemistry 34(11):2367-2370.
Neeley, W.E. et al. (1981). "An Instrument for Digital Matrix Photometry," Clinical Chemistry 27(10):1665-1668.
Non Final Office Action dated Apr. 12, 2011, for U.S. Appl. No. 11/311,667, filed Dec. 20, 2005, 8 pages.
Non Final Office Action dated Mar. 5, 2010, for U.S. Appl. No. 11/311,667, filed Dec. 20, 2005, 9 pages.
Non Final Office Action dated Apr. 8, 2015, for U.S. Appl. No. 13/566,886, filed Aug. 3, 2012, 12 pages.
Non-Final Office Action dated Mar. 20, 2017, by the United States Patent and Trademark Office for U.S. Appl. No. 15/191,434, filed Jun. 23, 2016, 20 pages.
Non-Final Office Action for U.S. Appl. No. 17/815,137 dated May 10, 2023, 19 pages.
Non-final Office Action issued in U.S. Appl. No. 12/983,078, dated Sep. 13, 2013, 12 pgs.
Non-final Office Action issued in U.S. Appl. No. 17/815,137, dated May 10, 2023, 18 pgs.
Non-final Office Action issued in U.S. Appl. No. 17/848,271, dated Aug. 31, 2022, 7 pgs.
Non-Final Office Action dated Aug. 10, 2018, for U.S. Appl. No. 14/311,114, filed Jun. 20, 2014, 15 pages.
Non-Final Office Action dated Dec. 16, 2016, for U.S. Appl. No. 13/566,886, filed Aug. 3, 2012, 11 pages.
Non-Final Office Action dated Apr. 28, 2009, for U.S. Appl. No. 11/529,613, filed Sep. 29, 2006, 22 pages.
Non-Final Office Action dated Aug. 19, 2015, for U.S. Appl. No. 14/311,114, filed Jun. 20, 2014, 15 pages.
Non-Final Office Action dated Aug. 7, 2020, for U.S. Appl. No. 15/697,311, filed Sep. 6, 2017, 10 pages.
Non-Final Office Action dated Dec. 12, 2007, for U.S. Appl. No. 11/529,613, filed Sep. 29, 2006, 14 pages.
Non-Final Office Action dated Jul. 8, 2015, for U.S. Appl. No. 12/457,331, filed Jun. 8, 2009, 13 pages.

(56) References Cited

OTHER PUBLICATIONS

Non-Final Office Action dated Jul. 8, 2021, for U.S. Appl. No. 16/215,468, filed Dec. 10, 2018, 11 pages.
Non-Final Office Action dated Jun. 13, 2014, for U.S. Appl. No. 12/457,331, filed Jun. 8, 2009, 8 pages.
Non-Final Office Action dated Jun. 25, 2015, for U.S. Appl. No. 12/457,332, filed Jun. 8, 2009, 7 pages.
Non-Final Office Action dated Jun. 4, 2010, for U.S. Appl. No. 11/529,613, filed Sep. 29, 2006, 24 pages.
Non-Final Office Action dated Mar. 20, 2019, for U.S. Appl. No. 15/499,821, filed Apr. 27, 2017, 12 pages.
Non-Final Office Action dated Mar. 8, 2017, for U.S. Appl. No. 14/311,114, filed Jun. 20, 2014, 11 pages.
Non-Final Office Action dated Nov. 23, 2011, for U.S. Appl. No. 12/457,331, filed Jun. 8, 2009, 7 pages.
Non-Final Office Action dated Nov. 27, 2019, for U.S. Appl. No. 15/697,311, filed Sep. 6, 2017, 7 pages.
Non-Final Office Action dated Oct. 15, 2020, for U.S. Appl. No. 15/499,821, filed Apr. 27, 2017, 15 pages.
Non-Final Office Action dated Sep. 29, 2017, for U.S. Appl. No. 15/499,821, filed Apr. 27, 2017, 10 pages.
Notice of Allowance for U.S. Appl. No. 17/848,271 dated Jan. 24, 2023, 5 pages.
Notice of Allowance issued in U.S. Appl. No. 15/499,821, dated Apr. 8, 2022, 7 pages.
Notice of Allowance issued in U.S. Appl. No. 16/215,468, dated Mar. 9, 2022, 6 pages.
Notice of Allowance dated Jun. 29, 2012, for U.S. Appl. No. 11/311,667, filed Dec. 20, 2005, 5 pages.
Notice of Allowance dated Aug. 18, 2017, for U.S. Appl. No. 13/566,886, filed Aug. 3, 2012, 10 pages.
Notice of Allowance dated Jan. 26, 2017, for U.S. Appl. No. 12/457,331, filed Jun. 8, 2009, 7 pages.
Notice of Allowance dated Mar. 4, 2021, for U.S. Appl. No. 15/697,311, filed Sep. 6, 2017, 9 pages.
Notice of Allowance dated May 15, 2019, for U.S. Appl. No. 12/457,332, filed Jun. 8, 2009, 8 pages.
Notice of Allowance dated May 3, 2011, for U.S. Appl. No. 11/529,613, filed Sep. 29, 2006, 6 pages.
Otto, E. et al. (2000). "An Intelligent Diabetes Software Prototype: Predicting Blood Glucose Levels and Recommending Regimen Changes," Diabetes Technology and Therapeutics 2(4):569-576.
Pfohl, M. et al. (2000). "Spot Glucose Measurement in Epidermal Interstitial Fluid—An Alternative to Capillary Blood Glucose Estimation," Experimental and Clinical Endocrinology & Diabetes 108(1):1-4.
Princen, H.M. (Jul. 1969). "Capillary Phenomena in Assemblies of Parallel Cylinders, II. Capillary Rise in Systems with More Than Two Cylinders," Journal of Colloid and Interface Science 30(3):359-371.
Princen, H.M. (May 1969). "Capillary Phenomena in Assemblies of Parallel Cylinders, I. Capillary Rise Between Two Cylinders," Journal of Colloid and Interface Science 30(1):69-75.
Rebrin, K. et al. (Sep. 1999). "Subcutaneous Glucose Predicts Plasma Glucose Independent of Insulin: Implications for Continuous Monitoring," American Journal of Physiology 277(3):E561-E571.
Restriction Requirement dated Dec. 22, 2011, for U.S. Appl. No. 12/457,332, filed Jun. 8, 2009, 6 pages.
Restriction Requirement dated Sep. 29, 2011, for U.S. Appl. No. 12/457,332, filed Jun. 8, 2009, 6 pages.
Rosen, S. (1999). "Road to New-Age Glucose Monitoring Still Rocky," Diagnostic Insight, pp. 4-5, 12-13, 16.
Smart, W.H. et al. (2000). "The Use of Silicon Microfabrication Technology in Painless Glucose Monitoring," Diabetes Technology & Therapeutics 2(4):549-559.
Sonntag, 0. (1993). Ektachem. Dry Chemistry, Analysis With Carrier-Bound Reagents, Elsevier Science Publishers, 57 pages.
Spielman, A. et al. (2001). Mosquito: A Natural History of Our Most Persistent and Deadly Foe, First Edition, Hyperion, New York, NY, 3 pages. (Table of Contents Only).
Straub F.B. (Mar. 1939). "Isolation and Properties of a flavoprotein from Heart Muscle Tissue", Biochemical Journal 33: 787-792.
Svedman, C. et al. (Apr. 1999). "Skin Mini-Erosion Technique for Monitoring Metabolites in Interstitial Fluid: Its Feasibility Demonstrated by OGTT Results in Diabetic and Non-Diabetic Subjects," Scand. J. Clin. Lab. Invest. 59(2): 115-123.
Tietz, N.W. (1986). Textbook of Clinical Chemistry, W. B. Saunders Company, pp. 1533 and 1556.
Trinder, P. (1969). "Determination of Glucose in Blood Using Glucose Oxidase with an Alternate Oxygen Acceptor," Annals of Clinical Biochemistry 6:24-28.
U.S. Precision Lens, Inc. (1983). The Handbook of Plastic Optics, 78 pages.
Wikipedia (2016). "Capillary action," 7 pages.
Written Opinion dated Jul. 28, 2009, for PCT Application No. PCT/US2009/003445, filed on Jun. 8, 2009, 4 pages.
Written Opinion dated Oct. 19, 2012 for PCT Application No. PCT/US2012/049629, filed on Aug. 3, 2012, 7 pages.
Written Opinion of the International Searching Authority dated Jul. 28, 2009, for PCT Application No. PCT/US2009/03441, filed on Jun. 8, 2009, 2 pages.
Written Opinion of the International Searching Authority dated Oct. 15, 2014 for PCT Application No. PCT/US2014/043516, filed on Jun. 20, 2014, 5 pages.
Yum, S. I. et al. (Nov. 1, 1999). "Capillary Blood Sampling for Self-Monitoring of Blood Glucose," Diabetes Technology & Therapeutics, 1 (1):29-37.

\* cited by examiner

MEDICAL DIAGNOSTIC DEVICES AND METHODS

CROSS-REFERENCE TO RELATED APPLICATIONS

This application is a continuation application of U.S. application Ser. No. 16/536,066, filed Aug. 8, 2019, now U.S. Pat. No. 11,553,860, which is a continuation application of U.S. application Ser. No. 12/457,332, filed on Jun. 8, 2009, now U.S. Pat. No. 10,383,556, which claims priority to U.S. Provisional Application No. 61/129,148, filed on Jun. 6, 2008.

FIELD

The present invention is directed to devices and methods possessing one or more of improved timekeeping abilities and functionality, and visual user interfacing capabilities.

BACKGROUND

In this specification where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

Currently, glucose monitors typically include a clock function that allows the device to mark each individual glucose measurement with a timestamp. As the user tests with the device over a period of time, the time data collected and the associated glucose values are used by the patient and their care givers to create charts of glucose measurements. This set of data can be used to adjust patient medication or as a tool to gauge effectiveness of current treatments.

A flaw in current systems is that they are dependent on the users to correctly set the time. Setting the time on a glucose meter is not always a straight forward task and many of the users of glucose meters are older and/or not technologically savvy. It is also very likely that many users of glucose meters are not even aware that they should be setting the time on their devices. The difficulty in correctly setting the time results in many glucose meters collecting inaccurate data that is not useable by patient or caregiver.

A problem with episodic glucose monitoring is that patients only get a snapshot of their current blood glucose. They must make treatment decisions using that snapshot, rather than using dynamic information that more accurately reflects their condition.

For example, if a patient tests and finds that their blood glucose is low, they may decide to take in some carbohydrates to raise their blood sugar. However, it may be that their glucose is already rising, in which case they may not need as much, or any carbohydrates.

Conversely, a patient may test and find that their blood glucose is at a desirable level, not realizing that their glucose is actually rapidly dropping. In this case they will probably decide not to intake any carbohydrates, when in reality they may face a hypoglycemic event soon if they don't act.

It would be desirable for the glucose meter to be able to forecast what direction and how quickly glucose levels are changing. This would allow the user to more accurately treat themselves, thus reducing the likelihood of hypoglycemic or hyperglycemic events.

In order to do such forecasting, at least two things are required: enough historical data in order to predict future trends; and accurate time-stamping information associated with those historical glucose results.

SUMMARY OF THE INVENTION

As used herein, "body fluid" encompasses whole blood, intestinal fluid, and mixtures thereof.

As used herein "integrated device" or "integrated meter" means a device or meter that includes all components necessary to perform sampling of body fluid, transport of body fluid, quantification of an analyte, and display of the amount of analyte contained in the sample of body fluid. Exemplary integrated meters are described in: U.S. Pat. Nos. 6,540,675 and 7,004,928; U.S. Patent Application Publication Nos. US 2008/0077048, US 2007/0179404, US 2007/0083131, US 2007/0179405, US 2007/0078358, and US 2007/0078313. The entire contents of each of the above-listed documents are incorporated herein by reference.

It is to be understood that reference herein to first, second, third and fourth components (etc.) does not limit the present invention to embodiments where each of these components is physically separable from one another. For example, a single physical element of the invention may perform the functions of more than one of the claimed first, second, third or fourth components. Conversely, a plurality of separate physical elements working together may perform the functions of one of the claimed first, second, third or fourth components. Similarly, reference to first, second (etc.) method steps does not limit the invention to only separate steps. According to the invention, a single method step may satisfy multiple steps described herein. Conversely, a plurality of method steps could, in combination, constitute a single method step recited herein. In addition, the steps of the method are not necessarily limited to the order in which they are described or claimed herein.

Advantages provided by the invention over the current technology may optionally include: guaranteeing that any device in which the technology is used will be able to automatically and accurately set the internal clock of the device to local time. When applied to a fully integrated glucose meter this invention may have one or more of the following specific advantages: convenience of never having to set time on the device; assurance that the device's internal clock will always be set to correct local time; significant increase in caregiver's confidence in data collected by meter; improved ability to monitor/detect trends in test results; ability to confidently adjust patient medications based on data collected by meter; allows meter to internally process data using methods not currently used in glucose monitors; can provide users with information not currently available on glucose meters; and providing the user with a clear and constant indication of the number of tests performed or remaining in an integrated meter.

According to a first aspect, the present invention provides a medical diagnostic device comprising means for receiving and processing time data transmitted wirelessly.

According to another aspect, the present invention provides a method for operating a medical diagnostic device, the method comprising: receiving and processing time data transmitted wirelessly.

According to a further aspect, the present invention provides a method of operating a blood glucose meter, the method comprising: receiving and processing time data transmitted wirelessly with the blood glucose meter; performing a plurality of tests with the blood glucose meter; correlating a plurality of glucose concentration measurement values derived from the tests with particular points in time or intervals of time during the day to establish a predetermined range of typical glucose measurement values associated with a particular point in time or time interval; and alerting the user when a measured glucose value falls outside of the predetermined range of typical glucose measurements.

According to yet another aspect, the present invention provides a method of monitoring and treating diabetes with the assistance of a blood glucose meter, the method comprising: receiving and processing time data transmitted wirelessly with the blood glucose meter; performing a plurality of tests with the blood glucose meter; correlating glucose concentration measurement values derived from the tests with the particular points in time during the day when they were taken to establish a data set; downloading the data set from the blood glucose meter; deriving trends based on the downloaded glucose concentration values and associated time data; and prescribing treatment based at least in part on the trends.

According to another alternative aspect, the present invention provides a method of monitoring and treating diabetes with the assistance of a blood glucose meter, the method comprising: receiving and processing time data transmitted wirelessly with the blood glucose meter; performing at least one test with the blood glucose meter thereby creating a blood glucose concentration measurement value; correlating the glucose concentration measurement value with the particular point in time during the day when the test was performed; and automatically identifying the glucose concentration measurement value as being associated with either a pre-prandial test or post-prandial test based at least in part on the correlated time associated with the value, or prompting the user to identify the glucose concentration measurement value as being associated with either a pre-prandial test or post-prandial test.

BRIEF DESCRIPTION OF THE DRAWING FIGURES

The following description of preferred embodiments can be read in connection with the accompanying drawings in which like numerals designate like elements and in which.

DETAILED DESCRIPTION

According to certain aspects, the present invention is aimed at a fully integrated glucose meter. However, the present invention is not be limited to integrated glucose meters because its benefits can also be applied to conventional (non-integrated) glucose meters, and other diagnostic devices where collection of long term data and analysis of trends in data is important. In the description that follows the term "device" is used to collectively refer to the abovementioned devices/implementations of the principles of the present invention.

Figure 1:
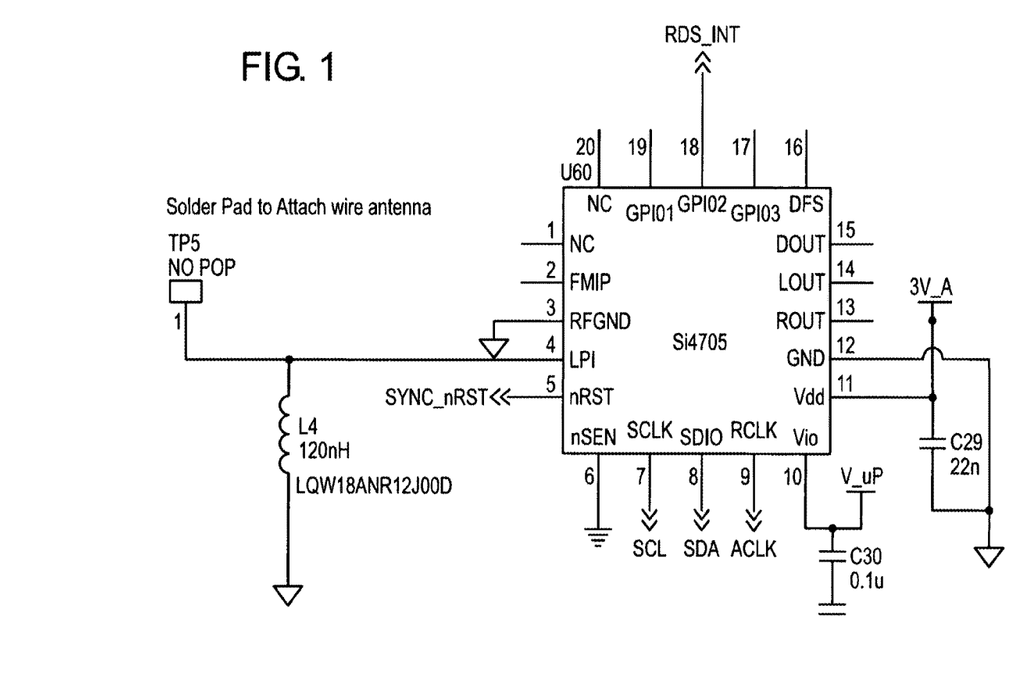
FIG. 1 is a schematic illustration of circuitry used to gather and process signals containing time data.

In general terms, when applied to a device, the invention enables the device to use time information commonly available in wireless communications (e.g., radio data system (RDS/RBDS), cell phone, WIFi, etc.) to automatically, quickly, and accurately adjust the internal clock of the device and set it to the correct local time. The invention may include electronic components that when combined give the meter access to time data transmitted wirelessly. Once the correct electronics are in place and the meter can access the information, the data must be carefully processed to ensure that the device is automatically programmed to the correct time. Many electronic components are available that allow access to data in the Radio Broadcast Data Stream (RDS/RBDS). One such component is Si4705 integrated circuit from Silicon Labs. FIG. 1 shows a schematic of such a component, and additional electrical components associated with gathering time data from the RBDS. In addition to the components illustrated in FIG. 1, an antenna may also be provided that allows the integrated circuit to receive RBDS information outdoors and indoors. The antenna can be a simple wire of a specific length optimized to receive RBDS data or any other antenna design to guarantee signal strengths in all intended use environments, homes, offices, cars, parks, etc.

In one alternative embodiment, the integrated circuit and associated electronics are integrated onto the main circuit board assembly of a device.

Collecting data is only one aspect of the invention. Once time data is being collected it is processed in a way that allows the device to accurately and efficiently translate the raw radio signal into a usable time. This involves both hardware and software processing of the signal. One optional method of converting a raw RBDS signal into the correct time on a device is illustrated in state diagram form in FIG. 2.

Figure 2:
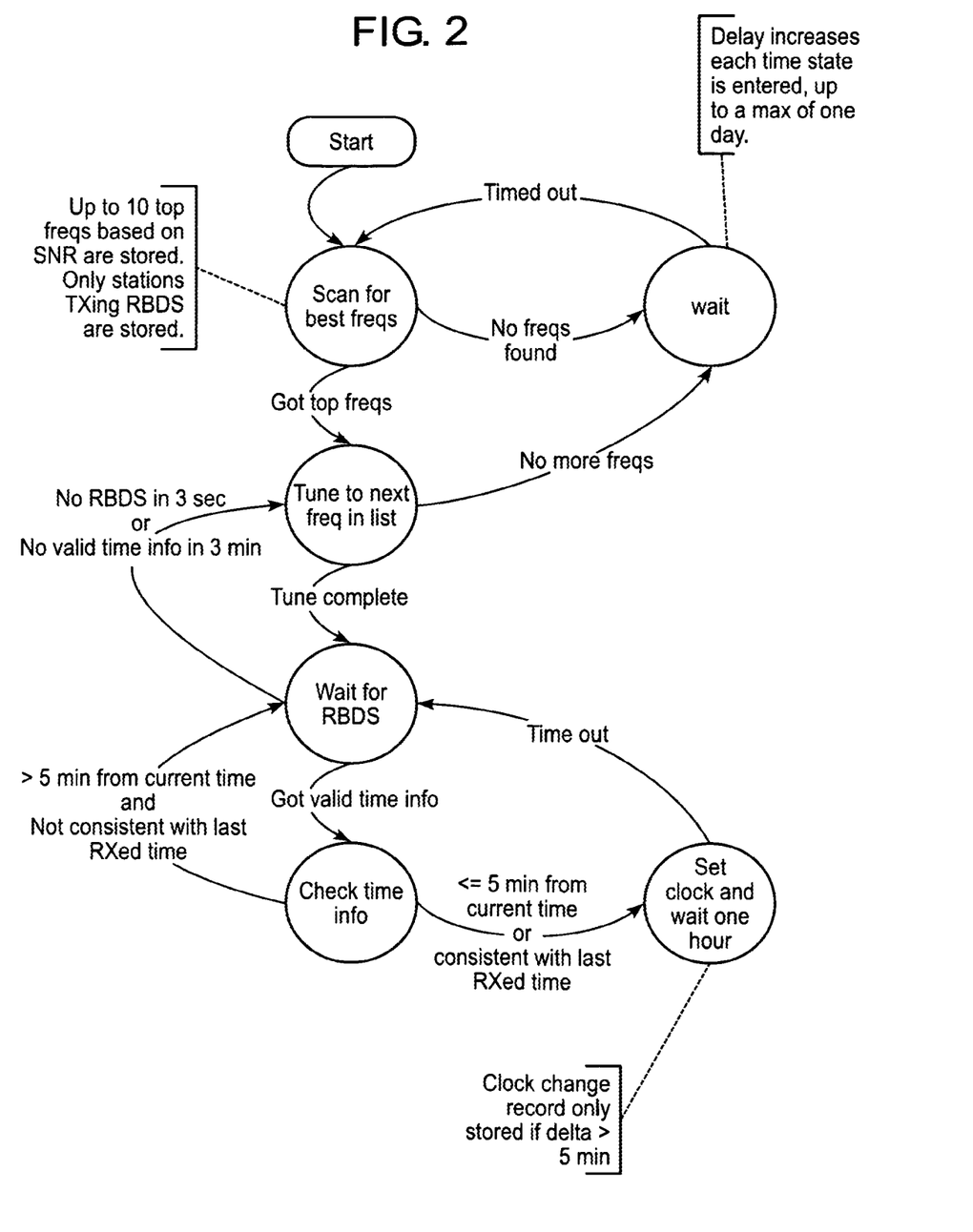
FIG. 2 is a state diagram illustrating methods whereby a diagnostic medical device may process a signal for use in generating accurate time data for use by the device.

A summary of what is described in the state diagram follows:

1. The device scans local area for a plurality (e.g., up to 10) best RBDS frequencies based on signal to noise ratio (SNR).
   a. Scanning for ten signals allows for redundancy should any signal be lost.
   b. Storing multiple frequencies as a data file also improves the speed at which RBDS time information can be acquired. If a particular frequency does not produce usable time data quickly the meter can change to another frequency without a delay in scanning all frequencies.
   c. Access to multiple signals also allow for a comparison of the time carried by several signals as a verification of having set the correct time on the device.
   d. Searching based on SNR ensures that the device can lock in to the signal sources that are nearest to it, and therefore set the correct time for the device's current position.
2. NOTE: To conserve power the device's firmware may also include instructions to incrementally increase the time between searching for useable frequencies if it encounters difficulty finding a useable signal.
   a. This is illustrated by the "wait" balloon in the top right section of the state diagram.

b. This algorithm maximizes battery life.
   i. Under certain conditions (shipping, storage, travel to very remote locations, etc.) a useable RBDS may be difficult to locate.
   ii. If the device's program logic was not intelligent enough to determine when to search for a signal it would continue to search until it exhausted its power supply.
3. Once the device has successfully created an internal database of usable RBDS frequencies it begins searching for valid time information.
4. After finding valid time information the device compares the time currently stored in the device with the time carried by the RBDS.
5. If the internally stored time is inconsistent with a verified RBDS time the clock is set to the RBDS time, the device then waits until the next time checking cycle arrives.

Accurately setting the internal clock is only one aspect of the invention. Additional features and benefits that an accurately set clock can provide to a device are also provided by the present invention. The following list is not meant to be exhaustive but is exemplary of some of the potential benefits.

Glucose forecasting will improve the safety of users of an analyte monitor by preventing improper intake of either food or medications.

Option 1—Use Most Recent Previous Test Data

If the user of a device frequently the device can look at the last few tests to determine if a trend can be identified. For example:

$$7 \text{ pm glucose} = 125 \text{ mg/dL} \rightarrow 8 \text{ pm glucose} = 68 \text{ mg/dL}$$

The device can identify this as a rapidly falling glucose and may alert the user to test again within a set period of time to verify the trend. It is also possible to suggest the user contact their care provider and/or suggest a potential treatment, such as carbohydrate intake.

Option 2—Historical Data

If the user of the device consistently tests around the same time period (i.e., upon waking, hour after lunch, etc.) the meter can "learn" the user's typical trends and suggest appropriate actions. For example, if the device consistently detects potential hypoglycemic events (very low glucose values) at a specific time of day, but on a particular occasion detects normal values at the same time the device may encourage the user to test again within a few minutes to verify that the user's glucose levels are normal and not quickly dropping.

The methods and uses of glucose forecasting are not limited to those previously mentioned.

Another use of a reliably accurate internal-clock is the ability to alert users to retest after an abnormal test result. For example if over a defined period of time the user of the device consistently has measured glucose levels within a particular range the device may "learn" the users typical trending. Once the device has learned the user's trends it may begin to expect particular glucose measurements during a particular time of day. If the user completes a glucose measurement that appears abnormal, i.e., out of typical range for time of day, the device may encourage the user to test again to verify the result. While it is possible that the user's glucose measurement may be out of a typical range due to diet, activity levels or response to medication, it also possible that the device may have miscalculated the real glucose value due to a problem with the device. A common benchmark for glucose monitors is the ability to provide glucose measurements that are accurate +/−20% for 90% of the number of tests. This benchmark demonstrates that the potential for the occasional incorrect glucose measurements is widely accepted.

Many people with diabetes are dependent on medications (oral insulin, injectable insulin, or other oral medications) and other treatment plans to maintain their glucose levels within safe and acceptable ranges. For example, a doctor may ask their patient to test immediately upon waking, and then test an hour after breakfast, lunch and dinner. The doctor may then ask their patient to bring their device to their next office visit. When the patient arrives with a device clinical staff may download all of the data that the meter has collected. This data is then analyzed using many methods to suggest appropriate treatment plans. One typical analysis is to plot all of the patient's glucose values compared to time of day. This results in a plot that shows how patient's glucose levels "trend" throughout the day. The clinical staff can then look the patient's trend plot to determine how much medication to prescribe and when to ask their patient to take the medications. This type of analysis can be very effective in helping patient maintain acceptable glucose levels throughout an entire day.

However, complications can arise if the patient's meter does not have correct time information. If the clinical staff notices that the device has the incorrect time they may be able to offset the data and adjust the trend plot so that treatment plans can still be adjusted. This type of adjustment is dependent on knowing how long the device's internal clock has been improperly set. For example, it would be completely unknown to the clinical staff if the patient's device had correct time for half the results, but then incorrect time for the second half of the results. The clinical staff seeing the incorrect time may then shift every result so that half of them are still incorrect. At best, the clinical staff may decide not to change treatment plans due to lack of confidence in the data. At worst, the clinical staff may incorrectly adjust the treatment plan and unknowingly put the patient at risk.

It is also possible that the clinical staff may not notice that the device has the incorrect time set and may read an incorrect trend plot and adjust the treatment plan incorrectly. Again, this can prevent a patient from improving their disease management or even put the patient at risk for over or under medicating.

Many patients with diabetes receive their treatments at either endocrinologists, or primary care doctors focused on working with these patients. The offices that treat patients with diabetes can therefore see several patients in a given day. To maintain an efficiently running office clinical staff need to quickly be able to collect information from patient's device, process the information, and provide data to the clinical staff to allow them to determine effectiveness of current treatments and create modified treatment plans to improve patient's disease management. The process of collecting data from patient's device is already very time and labor intensive. Each device currently on the market has its own individual data transfer cable and data transfer software. When a meter is processed for data download the clinical staff needs to identify the correct cable, the correct software and then hope that the transfer occurs without any issues. If the clinical staff is distracted by trying to figure out how to properly set the time on a device, valuable time will be wasted. Since every device on the market has an individual user interface, it is not uncommon that the clinical staff would have to look up how to adjust the device's clock in a users guide, wasting even more time. This invention ensures that patient's device is always set correctly and therefore will directly save time and money for clinics providing care for patients with diabetes.

Another way in which this invention provides a time and cost savings for clinics is by speeding up the training that each patient must get when receiving a new device. Currently, it is common practice for clinical staff (Certified Diabetes Educator, etc.) to spend time training each patient when they receive a new device. Such training typically includes basic meter operation, and some time spent setting up the device (user preferences, time of day, etc.). The removal of training for setting the clock will provide an instant time savings. This time saving may seem minimal, but when multiplied by the thousands of patients treated by a clinic every year it is very significant.

One of the key factors that clinical staff monitor in their patients while creating and maintaining treatment plans is the patient's glucose levels before and/or 1-2 hours after eating; these tests are typically called pre-prandial and post-prandial tests. This data can be extracted manually from the data collected by the device by looking at the time a test occurred and assuming it was before or after a particular meal. Another way of collecting this data relies on a feature that some devices have that allow user's to mark a particular test as either pre- or post-prandial. There are deficiencies in both methods.

If the data is manually extracted, the clinical staff must first assume that the time on the device was correct when the data was collected, then be comfortable assuming that data collected during a particular time was either pre or post-prandial, and also be able and willing to dedicate more time to a labor intensive data extraction process.

Data marked by the users of the device can be more accurate, however, this method only works if a user understands how to mark a test, selects the appropriate meal marker, i.e., pre- or post-breakfast, etc., remembers to mark all of their tests so that the averages created can have an accurate and sufficiently large data set.

Another benefit of this invention is that it enables a device to accurately and automatically mark tests as either pre- or post-prandial. The following is one of the many possible logic sequences or operational modes that will allow a device to automatically meal stamp a test.
1. The device automatically sets and maintains internal clock as previously described.
2. Option 1: The device can be automatically setup to group tests as pre- or post-meal depending on time of day
    a. Ex. Tests between 5-7 am are always marked as pre-breakfast and tests between 9-10 am are always marked as post-breakfast, etc.
3. Option 2: User can setup the device manually so that it "learns" when they have particular meals and use this data to automatically mark tests.
    a. Ex. User programs device once to know that tests between 6-8 am are pre-breakfast and tests between 9-11 am are post-breakfast, etc.
4. After a user completes a glucose measurement the device can compare the test's timestamp against the internal registry for pre- or post-meal times.
5. If a test falls within one of the meal time windows the device can automatically add a pre- or post-meal marker.
6. Optional: The device can automatically ask the user to verify that the test was pre- or post-meal. This is redundant but can add even more confidence to the dataset and will not require the user to navigate a confusing menu. A simple yes/no prompt is sufficient.
7. Optional: The device can store a continuously updating average of each pre- or post-meal glucose values.
    a. This average can be quickly accessed using a simple user interface directly on the device.
    b. Easy access to the data allows clinical staff to make well-informed treatment decisions without needing access to computers, cables, or additional software.

Figure 3:
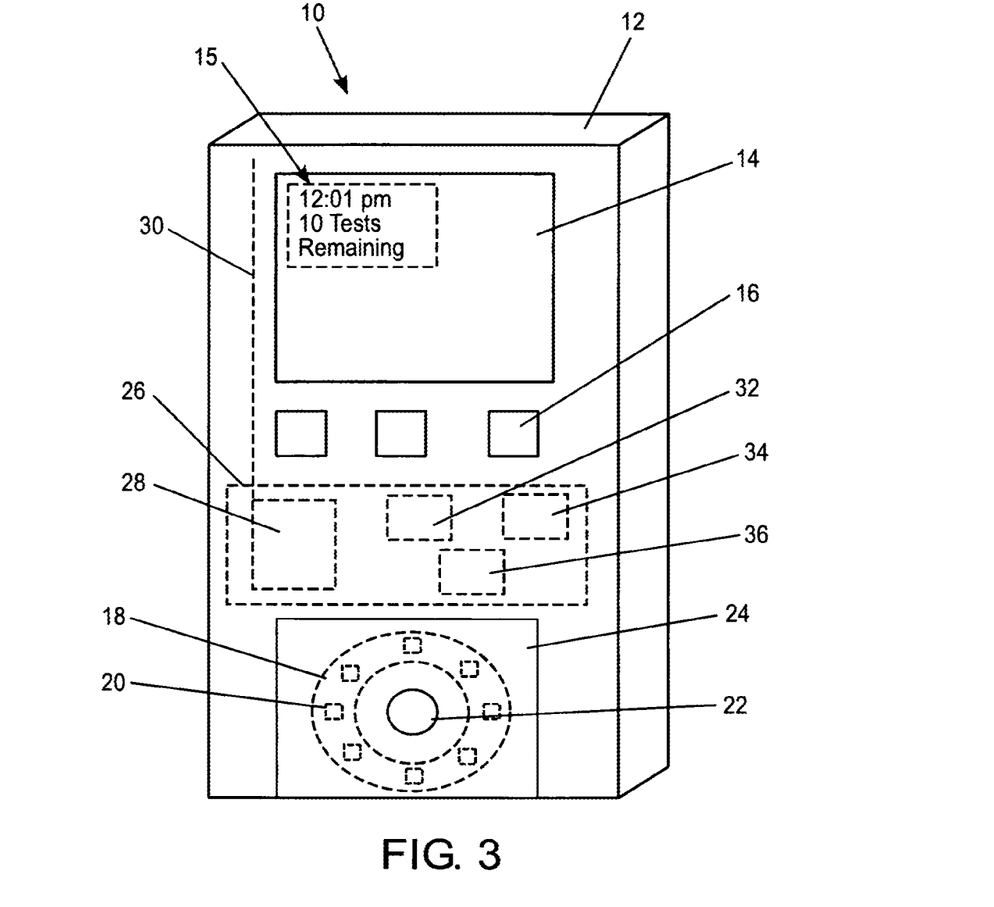
FIG. 3 is a schematic illustration of a diagnostic device constructed according to one optional aspect of the present invention.

A device formed according to further optional aspects of the present invention is illustrated in FIG. 3. The device 10 may comprise a housing 12 of any suitable form, formed of any suitable material. The device comprises a display 14. The device 10 can be provided with enhanced user interface functionality by providing a visual and/or audible signal of at least one of: the number of tests performed; and the number of test remaining to be performed, by the device. The device 10 may provided with one or more interface devices, such as buttons 16.

As alluded to above, a device 10 in the form of an integrated meter includes all of the necessary components for performing an assay to determine the concentration and/or presence of a target analyte. An integrated meter may in fact, according to the principles of the present invention, be provided with the necessary components for performing a plurality of tests, each capable of determining the presence and/or concentration of a target analyte substance. For example, an integrated meter may optionally be provided with a removable cartridge 18 or similar device which contains the necessary components 20 for performing a plurality of tests. The device 10 may comprise a test port 22 for accessing the components 20 of the cartridge 18 to perform a test. The cartridge may be removed through a door or cover 24 forming part of the housing 12. The number of tests which have been performed, or which are available for use before the cartridge 18 must be replaced, becomes important information to communicate to the user of such devices. According to the present invention, an integrated meter may be provided with the means necessary to produce a suitable audible and/or visual signal to the user to convey such information. Any suitable signal may be utilized. Suitable audible signals may include spoken information concerning the number of test performed and/or remaining. Suitable visual signals may include alphanumeric characters which specify the number of tests performed and/or remaining 15. These visual signals 15 may be continuously displayed by the integrated meter, even when the meter itself is "powered down" or otherwise shut off or placed in a "sleep" mode. According to a further alternative, the integrated meter may be designed such that it is inverted or flipped when it is to be applied to the skin of a user. Thus, according to a further aspect of the present invention, the device may include a suitable means for sensing is inverted or flipped condition and the visual display of alphanumeric characters may likewise be flipped or inverted so as to facilitate reading by the user, regardless of the orientation of the integrated meter.

The device 10 may further comprise a circuit board 26 comprising electronic components. These components may include components for receiving and processing time data transmitted wirelessly, as previously described herein Thus, the device 10 may comprise any of the functionality previously described herein. An integrated circuit 28 for receiving, and optionally at least partially processing, wirelessly transmitted time data may be provided. The integrated circuit 28 may take any suitable form, such as the Si4705 circuit commercially available from Silicon Labs, as previously described herein. The integrated circuit 28 may be provided with a suitable antenna 30, such as a wire-like antenna contained within the housing 12 of the device 10. Other suitable antennas are envisioned, such as external flexible antennas, and the like. The circuit board may further include a number of additional electronic components, such as a processor 32, memory 34 and power supply 36. The processor 32 may optionally cooperate with the integrated circuit 28, and may also process time data received thereby for use by the device 10.

Numbers expressing quantities of ingredients, constituents, reaction conditions, and so forth used in this specification are to be understood as being modified in all instances by the term "about". Notwithstanding that the numerical ranges and parameters setting forth, the broad scope of the subject matter presented herein are approximations, the numerical values set forth are indicated as precisely as possible. Any numerical value, however, inherently contains certain errors necessarily resulting from the standard deviation found in their respective measurement techniques. None of the elements recited in the appended claims should be interpreted as invoking 35 U.S.C. § 112, ¶6, unless the term "means" is explicitly used.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

We claim:

1. A method of operating a blood glucose meter, the method comprising:
   receiving and processing time data transmitted wirelessly with the blood glucose meter;
   performing a plurality of tests with the blood glucose meter;
   correlating a plurality of glucose concentration measurement values derived from the tests with particular points in time or intervals of time during the day to establish a predetermined range of typical glucose measurement values associated with a particular point in time or time interval; and
   alerting the user when a measured glucose value falls outside of the predetermined range of typical glucose measurements.

2. A method of monitoring and treating diabetes with the assistance of a blood glucose meter, the method comprising:
   receiving and processing time data transmitted wirelessly with the blood glucose meter;
   performing at least one test with the blood glucose meter thereby creating a blood glucose concentration measurement value;
   correlating the glucose concentration measurement value with the particular point in time during the day when the test was performed; and
   automatically identifying the glucose concentration measurement value as being associated with either a pre-prandial test or post-prandial test based at least in part on the correlated time associated with the value, or prompting the user to identify the glucose concentration measurement value as being associated with either a pre-prandial test or post-prandial test.

3. The method of claim 2, wherein the blood glucose meter comprises predefined time intervals associated with either a pre-prandial test or post-prandial test.

4. The method of claim 2, further comprising programming the blood glucose meter to define the pre-prandial test and post-prandial test time intervals.

5. A method of monitoring and treating diabetes with the assistance of a blood glucose meter, the method comprising:
   receiving and processing time data transmitted wirelessly with the blood glucose meter;
   performing a plurality of tests with the blood glucose meter;
   correlating glucose concentration measurement values derived from the tests with the particular points in time during the day when they were taken to establish a data set;
   downloading the data set from the blood glucose meter;
   deriving trends based on the downloaded glucose concentration values and associated time data; and
   prescribing treatment based at least in part on the trends.

6. A method for operating a medical diagnostic device, the method comprising:
   receiving and processing time data transmitted wirelessly, wherein receiving and processing time data comprises comparing time data currently stored within the device with time data obtained from at least one wireless time data transmission.

7. The method of claim 6, wherein receiving and processing time data further comprises overwriting the time data currently stored within the device with time data obtained from at least one wireless time data transmission upon detection of a discrepancy therebetween.

8. The method of claim 6, wherein the time data is transmitted via airwaves.

9. The method of claim 8, wherein the time data is transmitted from at least one of the following sources: radio broadcast data stream (RBDS); global positioning system (GPS); wireless fidelity network (WiFi); and the National Atomic Clock signal.

10. The method of claim 6, wherein receiving and processing time data comprises scanning the local area for wireless time data transmissions, calculating a signal-to-noise ratio for each wireless time data transmission received, and comparing the signal-to-noise ratio of a plurality of wireless time data transmissions received by the device.

11. The method of claim 10, wherein receiving and processing time data further comprises storing a plurality of frequencies as a data file.

12. The method of claim 10, wherein receiving and processing time data further comprises automatically and incrementally increasing the time between scanning the local area for wireless time data transmissions upon encountering difficulty in acquiring signals of a predetermined acceptable quality.

13. A medical diagnostic device comprising a wirelessly transmitted time data receiver and processor, wherein the receiver and processor are configured for scanning the local area for wireless time data transmissions, calculating a signal-to-noise ratio for each wireless time data transmission received, and comparing the signal-to-noise ratio of a plurality of wireless time data transmissions received by the device.

14. The device of claim 13, wherein the medical diagnostic device comprises an integrated glucose meter.

15. The device of claim 13, further comprising an antenna.

16. The device of claim 13, wherein the receiver and processor comprises an integrated circuit.

17. The device of claim 13, wherein the receiver and processor are further configured to store a plurality of frequencies as a data file.

18. The device of claim 13, wherein the receiver and processor are further configured to automatically and incrementally increase the time between scanning the local area for wireless time data transmissions upon encountering difficulty in acquiring signals of a predetermined acceptable quality.

19. The device of claim 13, wherein time data is transmitted via airwaves.

20. The device of claim 13, wherein time data is transmitted from at least one of the following sources: radio broadcast data stream (RBDS); global positioning system (GPS); wireless fidelity network (WiFi); and the National Atomic Clock signal.

21. The device of claim 13, wherein the receiver and processor are further configured to compare time data currently stored within the device with time data obtained from at least one wireless time data transmission.

22. The device of claim 21, wherein the receiver and processor are further configured to overwrite time data currently stored within the device with time data obtained from at least one wireless time data transmission upon detection of a discrepancy therebetween.

\* \* \* \* \*